US011787769B2

(12) United States Patent
Rong et al.

(10) Patent No.: US 11,787,769 B2
(45) Date of Patent: Oct. 17, 2023

(54) INHIBITORS OF INFLUENZA VIRAL ENTRY

(71) Applicants: Chicago Biosolutions, Inc., Chicago, IL (US); The Board of Trustees of the University of Illinois, Urbana, IL (US)

(72) Inventors: Lijun Rong, Westmont, IL (US); Irina Gaisina, Berwyn, IL (US); Gregory R. Thatcher, Tucson, AZ (US); Norton Peet, Chicago, IL (US)

(73) Assignees: THE BOARD OF TRUSTEES OF THE UNIVERSITY OF ILLINOIS, Urbana, IL (US); CHICAGO BIOSOLUTIONS, INC., Chicago, IL (US)

(*) Notice: Subject to any disclaimer, the term of this patent is extended or adjusted under 35 U.S.C. 154(b) by 0 days.

(21) Appl. No.: 17/735,235

(22) Filed: May 3, 2022

(65) Prior Publication Data

US 2022/0267275 A1 Aug. 25, 2022

Related U.S. Application Data

(63) Continuation of application No. PCT/US2020/059442, filed on Nov. 6, 2020.

(60) Provisional application No. 62/932,042, filed on Nov. 7, 2019.

(51) Int. Cl.
*C07D 215/58* (2006.01)
*A61P 31/16* (2006.01)
*A61K 31/47* (2006.01)
*A61K 45/06* (2006.01)

(52) U.S. Cl.
CPC ............ *C07D 215/58* (2013.01); *A61K 31/47* (2013.01); *A61K 45/06* (2013.01); *A61P 31/16* (2018.01)

(58) Field of Classification Search
CPC ....... C07D 215/58; A61P 31/16; A61K 31/47; A61K 45/06
See application file for complete search history.

(56) References Cited

U.S. PATENT DOCUMENTS

| | | | | | |
|---|---|---|---|---|---|
| 4,962,115 | A * | 10/1990 | Van Daele | C07D 211/58 | 546/224 |
| 5,057,525 | A * | 10/1991 | Van Daele | C07D 405/06 | 546/205 |
| 5,137,896 | A * | 8/1992 | Van Daele | C07D 233/56 | 514/327 |
| 8,524,736 | B2 * | 9/2013 | Irwin | A61P 1/14 | 546/137 |

FOREIGN PATENT DOCUMENTS

WO 2019004421 A1 1/2019

OTHER PUBLICATIONS

Gaisina, J Med Chem, 2020, vol. 63, 3120-3130. (Year: 2020).*
Hussein, Antiviral Research, vol. 177, 2020, 104782, pp. 1-8. (Year: 2020).*
Suryaprakash Sambhara and Gregory A. Poland, Title: H5N1 Avian Influenza:Preventive and Therapeutic Strategies Against a Pandemic, Annual Review Medicine vol. 61, 2010. pp. 187-88.
Ronald B. Moss et al, Title: Targeting pandemic influenza: a primer on influenza antivirals and drug resistance, Journal of Antimicrobial Chemotherapy, Published by Oxford University Press, 2010, pp. 1086-1093.
Vanderlinden et al. Title: Novel Inhibitors of Influenza Virus Fusion: Structure-Activity Relationship and Interaction with the Viral Hemagglutinin, Journal of Virology, May 2010, pp. 4277-4288, vol. 84, No. 9.
Plotch et al. Title: Inhibition of Influenza A Virus Replication by Compounds Interfering with the Fusogenic Function of the Viral Hemagglutinin†, Journal of Virology, Jan. 1999, p. 140-151, vol. 73, No. 1.
Wang et al., Title: A Comparative High-Throughput Screening Protocol to Identify Entry Inhibitors of Enveloped Viruses, Author manuscript, J Biomol Screen, Jan. 2014 vol. 19 pp. 100-107.
Shah et al. Title: Synthesis and evaluation of CCR5 antagonists containing modified 4-piperidinyl-2-phenyl-1-(phenylsulfonylamino)-butane, Bioorganic & Medicinal Chemistry Letters 15, 2005, pp. 977-982.
Manicassamy et al. Title: Comprehensive Analysis of Ebola Virus GP1 in Viral Entry, Journal of Virology, Apr. 2005, pp. 4793-4805, vol. 79, No. 8.
Manicassamy and Rong, Title: Expression of Ebolavirus glycoprotein on the target cells enhances viral entry, Virology Journal, 2009, Published Jun. 8, 2009 pp. 6-75.
Guo et al. Title: Analysis of hemagglutinin-mediated entry tropism of H5N1 avian influenza, Virology Journal, Bio Med Central, Published Apr. 2, 2009, pp. 6-39.
Zhao et al. Title: A Mechanism Underlying Attenuation of Recombinant Influenza A Viruses Carrying Reporter Genes, Viruses 2018, 10, 679, Published Nov. 30, 2018.
Xiujuan Zhao et al. Title: A Parallel Phenotypic Versus Target-Based Screening Strategy for RNA-Dependent RNA Polymerase Inhibitors of the Influenza A Virus, Viruses 2019, 11, 826, Sep. 4, 2019 Published.

(Continued)

*Primary Examiner* — D Margaret M Seaman
(74) *Attorney, Agent, or Firm* — Flener IP & Business Law; Zareefa B. Flener

(57) ABSTRACT

Vaccination is the most prevalent prophylactic means for controlling seasonal influenza infections. However, an effective vaccine usually takes at least 6 months to develop for the circulating strains. Therefore, new therapeutic options are needed for acute treatment of influenza infections to control this virus and prevent epidemic/pandemic situations from developing. Described herein are fast-acting, orally active acylated amino-substituted heterocyclyl compounds effective to control this virus. In one aspect, described herein is a method of treating an influenza infection in a subject comprising administering to the subject the compounds described herein.

15 Claims, 1 Drawing Sheet

(56) References Cited

OTHER PUBLICATIONS

Li et al. Title: A Simple and Robust Approach for Evaluation of Antivirals Using a Recombinant Influenza Virus Expressing Gaussia Luciferase, Viruses 2018, 10, 325 Published Jun. 18.
UKIPO Examination Report under section 18(3) for serial No. GB2206782.1; dated Apr. 19, 2023.
Irina N. Gaisina; Optimization of 4-Aminopiperidines as Inhibitors of Influenza A Viral Entry That are Synergistic with Oseltamivir; J. Med. Chem. 2020, 63, 3120-3130.
Lars Jorgensen; Structure-Activity Relationship, Pharmacological Characterization, and Molecular Modeling of Noncompetitive Inhibitors of the Betaine/γ-Aminobutyric Acid Transporter 1 (BGT1); J. Med. Chem. 2017, 60,8834-8846.
PubChem; 3-bromo-2-chloro-N-(1,3-dimethylpiperidin-4-yl) benzamide; avaliable at https://pubchem.ncbi.nlm.nih.gov/compound/113363364; the page was created in Jan. 28, 2016.
G Daidone; One-step synthesis, crystallographic studies and antimicrobial activity of new 4-diazopyrazole derivatives; J. Med. Chem (1996) 31, 461-468.
International Search Report for PCT/US2020/059442, dated Mar. 2, 2021.
Written Opinion of the International Searching Authority for PCT/US2020/059442, dated Mar. 2, 2021.
PubChem; 2-chloro-N-(1,3-dimethylpiperidin-4-yl)-4-nitrobenzamide; avaliable at https://pubchem.ncbi.nlm.nih.gov/compound/49623619; the page was created Nov. 26, 2010.

* cited by examiner

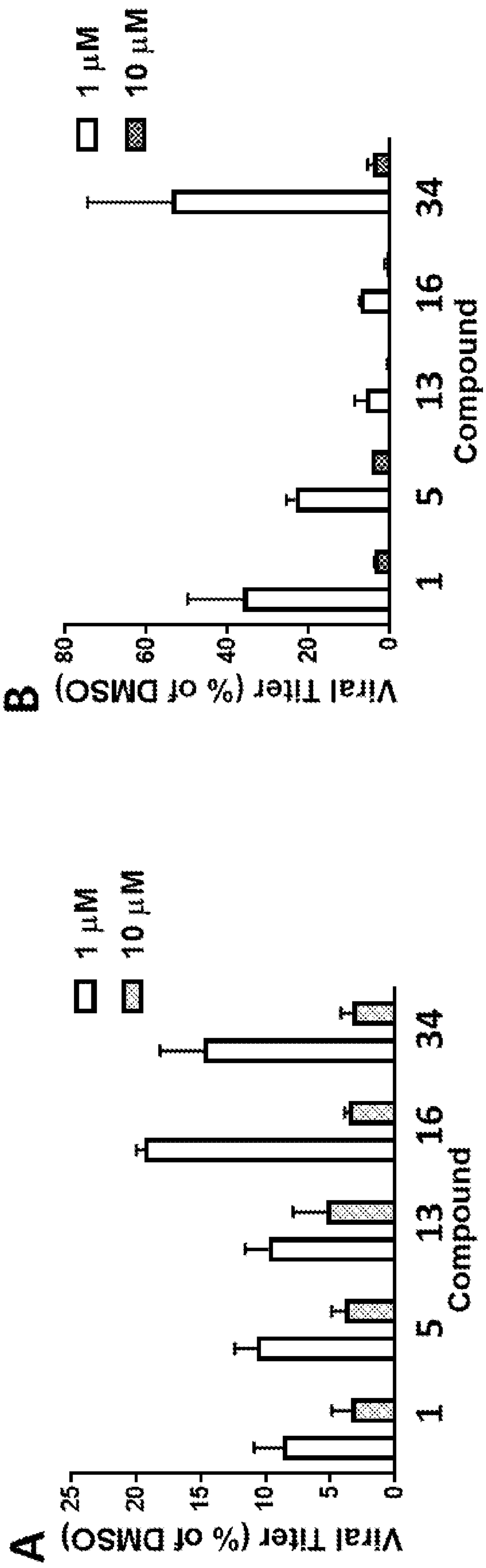
A
Viral Titer (% of DMSO)
0
5
10
15
20
25
1
5
13
16
34
Compound
1 μM
10 μM
B
Viral Titer (% of DMSO)
0
20
40
60
80
1
5
13
16
34
Compound
1 μM
10 μM

INHIBITORS OF INFLUENZA VIRAL ENTRY

CROSS REFERENCE TO RELATED APPLICATIONS

This application claims priority upon U.S. provisional application Ser. No. 62/932,042 filed on Nov. 7, 2019. This application is hereby incorporated by reference in its entirety.

STATEMENT OF GOVERNMENTAL INTEREST

This invention was made with government support under grant number R41AI127031 awarded by the National Institutes of Health. The government has certain rights in this invention.

TECHNICAL FIELD

Described herein are compounds that modulate influenza virus entry into the host cells. More particularly, described herein are fast-acting, orally-active acylated amino-substituted heterocyclyl compounds for use as anti-influenza therapeutics. Also disclosed are methods of treating influenza infections.

BACKGROUND

Seasonal or pandemic flu is an infectious disease that is mainly caused by influenza A viruses (IAV). Influenza A virus is under continuous evolvement due to antigenic mutation, adaptation, and reassortment, and highly virulent strains may appear unexpectedly to produce epidemics or pandemics. Vaccination remains the principal prophylactic for controlling influenza infections[1-3] although its efficacy is limited during a pandemic.[4-5] The neuraminidase inhibitors (NAIs) oseltamivir, zanamivir, and peramivir are the only therapeutic options in the response plans for new influenza outbreaks, while the influenza M2 ion channel blockers (amantadine and rimantadine) are not recommended anymore since all of the circulating influenza strains are resistant to them.[6-11] The efficacy of the NAIs has also been undermined by resistance.[12-14] More importantly, during the 2008-2009 influenza season, almost all seasonal influenza $A/H_1N_1$ isolates in the US were resistant to oseltamivir (99%, compared to 11% in 2007-2008).[15-18] The pandemic 2009 influenza $A/H_1N_1$ virus and the highly pathogenic avian influenza (HPAI) $H_5N_1$ strains have been generally susceptible to NAIs;[18-21] however, oseltamivir resistant strains have been isolated from patients infected with both of these strains.[18-23] Therefore, NAIs may not be sufficient for use alone in future influenza pandemics. Additional therapeutic agents with a new mechanism of action that are effective in treating influenza virus, either alone or in combination with other drugs are in great need.

SUMMARY

Vaccination is the most prevalent prophylactic means for controlling seasonal influenza infections. However, an effective vaccine usually takes at least 6 months to develop for the circulating strains. Therefore, new therapeutic options are needed for acute treatment of influenza infections to control this virus and prevent epidemic/pandemic situations from developing. Described herein are fast-acting, orally active acylated amino-substituted heterocyclyl compounds effective to control this virus.

Accordingly, in an aspect, described herein are compounds of formula I, or a pharmaceutically acceptable salt thereof

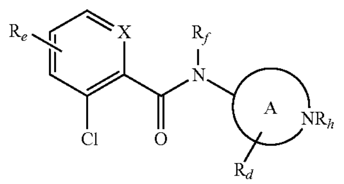

I wherein X is CH or N; ring A is a nitrogen-containing heterocyclyl; $R_h$ is alkyl or cycloalkyl; $R_d$ is one to nine substituents independently selected from alkyl, halo, haloalkyl, aryl, arylalkyl and $C_3$-$C_5$ cycloalkyl; $R_f$ is selected from H, alkyl, aryl, and arylalkyl; and $R_e$ is one to five substituents independently selected from halo, haloalkyl, aryl, arylalkyl and $-NO_2$.

In another aspect, described herein is a composition comprising a compound of formula I and a pharmaceutically acceptable excipient.

In another aspect, described herein is a method of treating an influenza infection in a subject comprising administering to the subject a compound of formula I.

In another aspect, described herein is a method of treating an influenza infection in a subject comprising administering to the subject a compound of formula I and a neuraminidase inhibitor.

In one aspect, the compounds described herein act as potent inhibitors of the oseltamivir-resistant influenza A $(H_1N_1)$ virus strain with the most common H274Y resistance mutation.

BRIEF DESCRIPTION OF THE DRAWINGS

FIG. 1 shows an infectious virus replication inhibition assay. $H_1N_1$ (A/Puerto Rico/8/1934) (A) or $H_5N_1$ (A/Vietnam/1203/2004) (B) viruses at the MOI of 0.01 were used to infect A549 cells in the presence or absence of selected 4-aminopiperidines at the 1 and 10 μM concentrations. At 48 h post-infection, viral titers were determined by the standard plaque assay in MDCK cells. The assay was performed in triplicate; results are presented as mean±SD.

DETAILED DESCRIPTION

Before the present materials, articles, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a neuraminidase inhibitor" includes mixtures of two or more such neuraminidase inhibitor, and the like.

"Optional" or "optionally" means that the subsequently described event or circumstance can or cannot occur, and that the description includes instances where the event or circumstance occurs and instances where it does not.

As used herein, the term “about” is used to provide flexibility to a numerical range endpoint by providing that a given value may be “a little above” or “a little below” the endpoint without affecting the desired result. For purposes of the present disclosure, “about” refers to a range extending from 10% below the numerical value to 10% above the numerical value. For example, if the numerical value is 10, “about 10” means between 9 and 11 inclusive of the end-points 9 and 11.

Throughout this specification, unless the context dictates otherwise, the word “comprise,” or variations such as “comprises” or “comprising,” will be understood to imply the inclusion of a stated integer or step or group of integers or steps, but not the exclusion of any other integer or step or group of integers or steps. It is also contemplated that the term “comprises” and variations thereof can be replaced with other transitional phrases such as “consisting of” and “consisting essentially of.”

“Admixing” or “admixture” refers to a combination of two components together when there is no chemical reaction or physical interaction. The terms “admixing” and “admixture” can also include the chemical interaction or physical interaction among any of the components described herein upon mixing to produce the composition. The components can be admixed alone, in water, in another solvent, or in a combination of solvents.

The term “subject” as defined herein is any organism in need of treatment and/or prevention (e.g., infection, inflammation, etc.). In one aspect, the subject is a mammal including, but not limited to, humans, domesticated animals (e.g., dogs, cats, horses), livestock (e.g., cows, pigs), and wild animals.

References in the specification and concluding claims to parts by weight, of a particular element in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound. A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an illustration, a numerical range of “about 1 to about 5” should be interpreted to include not only the explicitly recited values of about 1 to about 5, but also to include individual values and sub-ranges within the indicated range. Thus, included in this numerical range are individual values such as 2, 3, and 4, sub-ranges such as from 1-3, from 2-4, from 3-5, etc., as well as 1, 2, 3, 4, and 5, individually. The same principle applies to ranges reciting only one numerical value as a minimum or a maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a compound as described herein is disclosed and discussed and a number of different the neuraminidase inhibitors are discussed, each and every combination of compound and the neuraminidase inhibitor that is possible is specifically contemplated unless specifically indicated to the contrary. For example, if a class of molecules A, B, and C are disclosed, as well as a class of molecules D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Definitions

The following terms and expressions used herein have the indicated meanings.

Terms used herein may be preceded and/or followed by a single dash, “-”, or a double dash, “=”, to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read “left to right” unless a dash indicates otherwise. For example, $C_1$-$C_6$alkoxycarbonyloxy and —OC(O)$C_1$-$C_6$ alkyl indicate the same functionality; similarly arylalkyl and—alkylaryl indicate the same functionality.

“Alkenyl” means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

"Alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkyl" means a straight or branched chain hydrocarbon containing from 1 to 10 carbon atoms unless otherwise specified. The alkyl may be substituted with one or more groups selected from halo, hydroxy, alkoxy, cyano, amino, carboxyl and carboxyalkyl. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to $—CH_2—$, $—CH_2CH_2—$, $—CH_2CH_2CHC(CH_3)—$, and $—CH_2CH(CH_2CH_3)CH_2—$.

"Aryl" means a phenyl (i.e., monocyclic aryl), or a bicyclic ring system containing at least one phenyl ring or an aromatic bicyclic ring containing only carbon atoms in the aromatic bicyclic ring system. In certain embodiments of the disclosure, the aryl group is phenyl or naphthyl. In certain embodiments, the aryl is substituted with one or more groups selected from alkyl, cycloalkyl, cycloalkylalkyl, halo, haloalkyl, —CN, $—CO_2H$, $—SO_2R_h$, $—SO_2NHR_h$, $—NHSO_2R_h$ and heterocyclyl wherein $R_h$ is alkyl. In certain other embodiments, the aryl is phenyl.

"Arylalkyl" means an aryl group as defined herein connected to the parent molecular moiety through an alkylene group. An exemplary arylalkyl group is benzyl.

"Cyano" and "nitrile" mean a —CN group.

"Cycloalkyl" means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form $—(CH_2)_w—$, where w is 1, 2, or 3). Representative examples of bicyclic ring systems include, but are not limited to, bicyclo[3.1.1]heptane, bicyclo[2.2.1]heptane, bicyclo[2.2.2] octane, bicyclo[3.2.2]nonane, bicyclo[3.3.1] nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. In certain embodiments, the cycloalkyl is substituted with one or more groups selected from alkyl, cycloalkyl, cycloalkylalkyl, halo, haloalkyl, —CN, $—CO_2H$, $—SO_2R_h$, $—SO_2NHR_h$, $—NHSO_2R_h$ and heterocyclyl wherein $R_h$ is alkyl. In certain embodiments, the cycloalkyl is a $C_3$-$C_5$ cycloalkyl.

"Nitrogen-containing hetercyclyl" means a monocyclic or a bicyclic cycloalkyl ring system where one or more of the carbon atoms of the cycloalkyl ring is substituted with nitrogen. Monocyclic nitrogen-containing hetercyclyl ring systems are cyclic hydrocarbon groups containing from 3 to 8 carbon atoms and one or more nitrogen atoms, where such groups can be saturated or unsaturated, but not aromatic. In certain aspects, the nitrogen-containing hetercyclyl groups are fully saturated. Examples of monocyclic nitrogen-containing hetercyclyl groups include cyclopropyl, cyclobutyl, cyclopentyl, cyclopentenyl, cyclohexyl, cyclohexenyl, cycloheptyl, and cyclooctyl, where one or more carbon atoms is substituted with nitrogen.

Bicyclic nitrogen-containing hetercyclyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form $—(CH_2)_w—$, where w is 1, 2, or 3). Representative examples of bicyclic nitrogen-containing hetercyclyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, where one or more carbon atoms are substituted with nitrogen. Fused bicyclic nitrogen-containing hetercyclyl ring systems contain a monocyclic cycloalkyl ring fused to either a phenyl, a monocyclic cycloalkyl, a monocyclic cycloalkenyl, a monocyclic heterocyclyl, or a monocyclic heteroaryl, where one or more carbon atoms are substituted with nitrogen. The bridged or fused bicyclic cycloalkyl is attached to the parent molecular moiety through any carbon atom contained within the monocyclic cycloalkyl ring. In certain embodiments, the nitrogen-containing hetercyclyl is substituted with one or more groups selected from alkyl, cycloalkyl, cycloalkylalkyl, halo, haloalkyl, —CN, $—CO_2H$, $—SO_2R_j$, $—SO_2NHR_3$, $—NHSO_2R_j$ and heterocyclyl wherein $R_j$ is alkyl. In certain embodiments, the cycloalkyl is a $C_3$-$C_5$ cycloalkyl. In one aspect, the nitrogen-containing hetercyclyl selected from tetrahyroquinolyl, indolyl, indolinyl and piperidinyl;

"Halo" or "halogen" means —Cl, —Br, —I or —F.

"Haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl. In certain embodiments, each "haloalkyl" is a fluoroalkyl, for example, a polyfluoroalkyl such as a substantially perfluorinated alkyl.

"Saturated" as used herein means the referenced chemical structure does not contain any multiple carbon-carbon bonds. For example, a saturated cycloalkyl group as defined herein includes cyclohexyl, cyclopropyl, and the like.

"Unsaturated" means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

"Pharmaceutically acceptable salts" refers to salts or zwitterionic forms of the present compounds. Salts of the present compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present disclosure appearing herein is intended to include the present compounds as well as pharmaceutically acceptable salts thereof.

The following abbreviations shall have the indicated meaning: MSA, Bismuth sulfite agar; CI, Combination Index; DMEM, Dulbecco's Modified Eagle Medium; eGFP, enhanced green fluorescent protein; ESI, electrospray ionization; HA, hemagglutinin; HPAI, highly pathogenic avian influenza; IAV, influenza A virus; LC-MSD, liquid chromatography/mass selective detector; LM, liver microsomes; MDCK, Madin-Darby canine kidney; MOI, multiplicity of infection; NADPH, nicotinamide adenine dinucleotide phosphate, reduced form; NAI, neuraminidase inhibitor; PBS, phosphate buffered saline; STAB, sodium triacetoxyborohydride; TLC, thin layer chromatography; TPCK, N-p-tosyl-L-phenylalanine chloromethyl ketone.

Disclosed herein are new anti-influenza therapeutics to target the hemagglutinin (HA) that mediates influenza virus entry into the host cells.[24-27] HA is an attractive target because it is involved in the first step in viral entry and because HA-neutralizing antibodies are protective.[1,22,27-31] The HA inhibitors described herein may be used alone, or in combination with NAIs to treat infections by $H_1N_1$ and $H_5N_1$.

In one aspect, the compounds described herein or a pharmaceutically acceptable salt thereof have the structure I

I

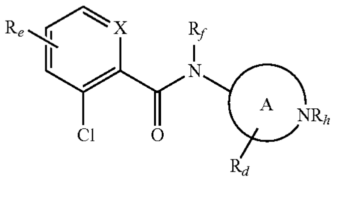

wherein

X is CH or N;

ring A is a nitrogen-containing hetercyclyl;

$R_h$ is alkyl or cycloalkyl;

$R_d$ is one to nine substituents independently selected from alkyl, halo, haloalkyl, aryl, arylalkyl and $C_3$-$C_5$ cycloalkyl;

$R_f$ is selected from H, alkyl, aryl, and arylalkyl; and $R_e$ is one to five substituents independently selected from halo, haloalkyl, aryl, arylalkyl and —$NO_2$.

In one aspect, the compounds described herein or a pharmaceutically acceptable salt thereof have the structure II

II

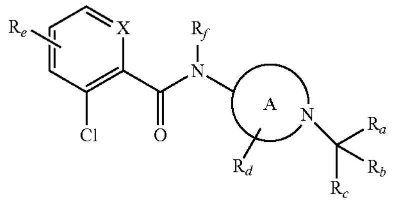

wherein X is CH or N; ring A is a nitrogen-containing hetercyclyl selected from tetrahyroquinolyl, indolyl, indolinyl and piperidinyl; $R_a$, $R_b$ and $R_c$ are independently selected from H, alkyl and aryl, or any two of $R_a$, $R_b$ and $R_c$, together with the C atom to which they are attached define a cycloalkyl; $R_d$ is one to nine substituents independently selected from alkyl, halo, haloalkyl, aryl, arylalkyl and $C_3$-$C_5$ cycloalkyl; $R_f$ is selected from H, alkyl, aryl, and arylalkyl; and $R_e$ is one to five substituents independently selected from halo, haloalkyl, aryl, arylalkyl and —$NO_2$.

In certain aspects, the compound of formula I is selected from

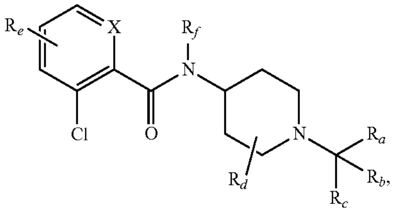

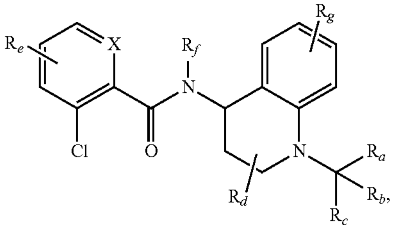

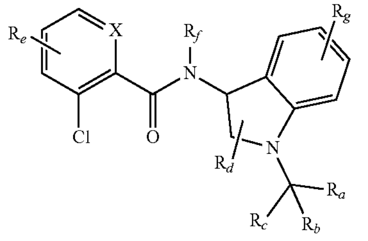

and

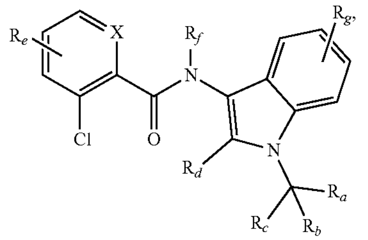

wherein Rg is one to four substituents independently selected from halo, haloalkyl, aryl, arylalkyl and $C_3$-$C_5$ cycloalkyl, or a pharmaceutically acceptable salt thereof.

In other aspects, X is CH.
In other aspects, $R_f$ is H.
In other aspects, $R_e$ is selected from —$NO_2$, Cl and —$CF_3$.
In other aspects, Rd is selected from H and halo and Rg is selected from H, halo, haloalkyl and $C_3$-$C_5$ cycloalkyl.
In other aspects, halo is F and haloalkyl is $CF_3$.
In another aspect, the compound of formula I is selected from
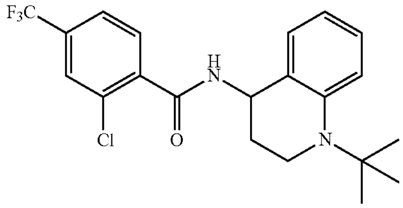
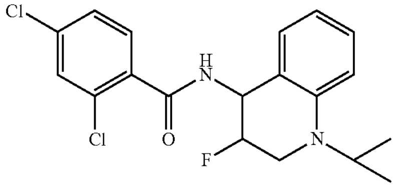
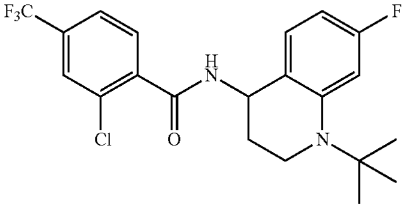
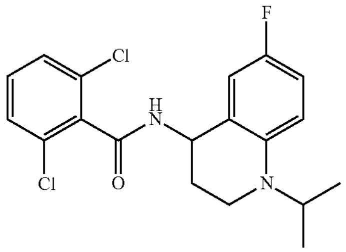
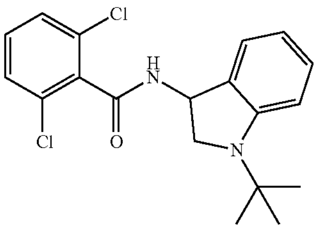
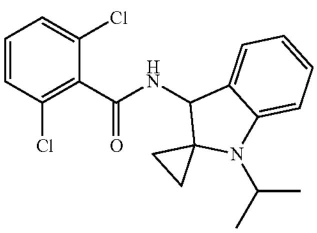
-continued
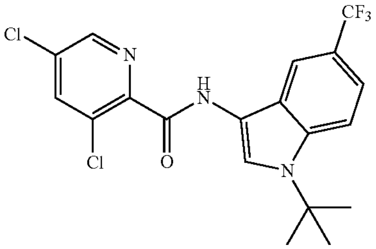
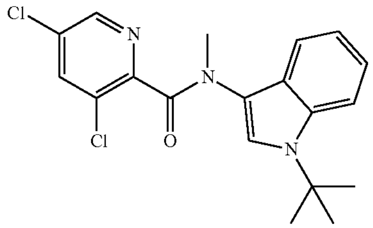
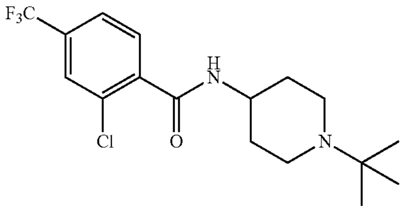
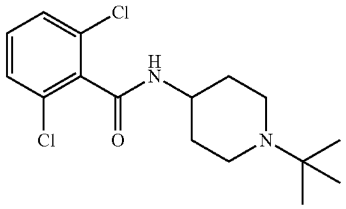
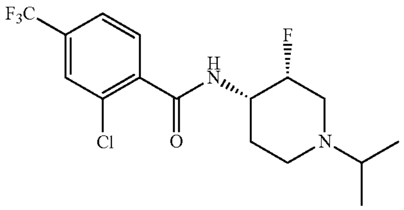
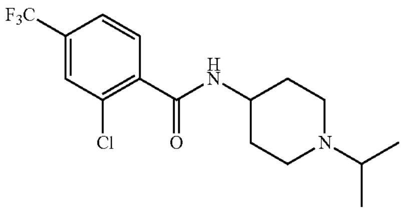
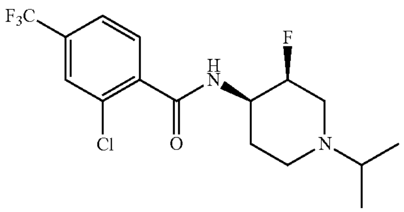

-continued

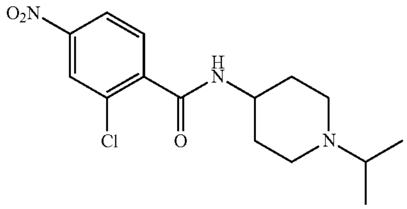

or a pharmaceutically acceptable salt thereof.

In other particular embodiments, the compound of formula I is selected from

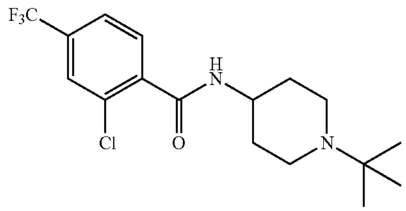

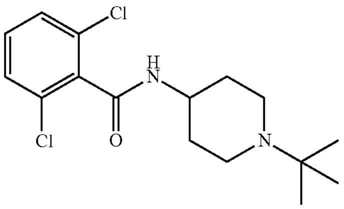

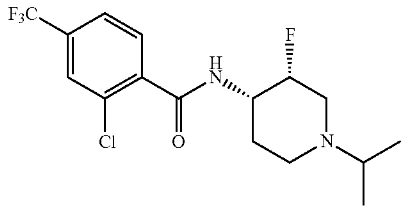

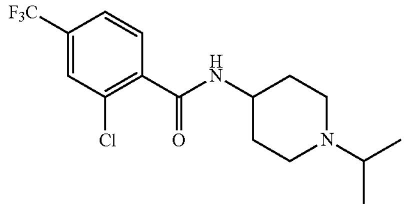

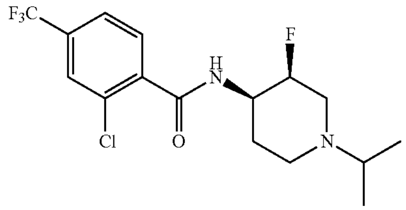

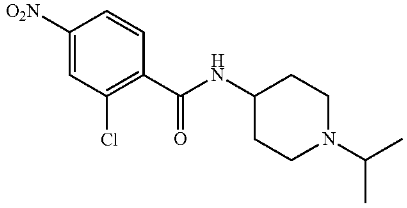

or a pharmaceutically acceptable salt thereof.

In one aspect, the compound has the structure

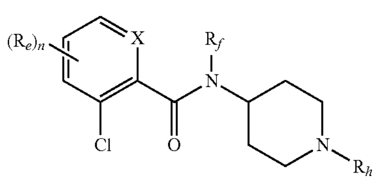

wherein $R_e$ is haloalkyl, X is CH, and n is 1 to 4. In another aspect, $R_e$ is haloalkyl, X is CH, and $R_f$ is H. In another aspect, $R_e$ is haloalkyl, X is CH, $R_f$ is H, and $R_h$ is an alkyl. In another aspect, n is 1. In another aspect, $R_e$ is $CF_3$. In another aspect, $R_e$ is at the 4 position of the aryl ring. In another aspect, $R_h$ is a tert-butyl group or an isopropyl group.

In one aspect, described herein is a method of treating an individual suffering from an influenza infection comprising administering a compound of structural formula (I) to an individual in need thereof.

The methods described herein relate to the use of a compound of formula I and an optional second therapeutic agent useful in the treatment of an influenza infection. The methods described herein can be accomplished by administering a compound of formula (I) as the neat compound or as a pharmaceutical composition. Administration of a pharmaceutical composition, or a neat compound of structural formula (I), can be performed during or after the onset of the disease or condition of interest.

In certain aspects, a compound of formula I is administered in conjunction with a second therapeutic agent useful in the treatment of influenza infections. The second therapeutic agent is different from the compound of formula I. A compound of structural formula I and the second therapeutic agent can be administered simultaneously or sequentially. In addition, a compound of formula I and the second therapeutic agent can be administered from a single composition or two separate compositions. A compound of formula I and the second therapeutic agent can be administered simultaneously or sequentially to achieve the desired effect.

In one aspect, the second therapeutic agent includes a neuraminidase inhibitor. Neuraminidase inhibitors (NAIs) are a class of drugs which block the neuraminidase enzyme. They are commonly used as antiviral drugs because they block the function of viral neuraminidases of the influenza virus, by preventing its reproduction by budding from the host cell. Oseltamivir (Tamiflu) a prodrug, Zanamivir (Relenza), Laninamivir (Inavir), and Peramivir belong to this class. In certain aspect, one or more neuraminidase inhibitors can be administered in conjunction with the compounds described herein.

The second therapeutic agent is administered in an amount to provide its desired therapeutic effect. The effective dosage range for each second therapeutic agent is known in the art, and the second therapeutic agent is administered to an individual in need thereof within such established ranges.

"Treating" or "treatment" includes the treatment of a disease or disorder described herein, in a subject, preferably a human, and includes: i. inhibiting a disease or disorder, i.e., arresting its development; ii. relieving a disease or disorder, i.e., causing regression of the disorder; iii. slowing progression of the disorder; and/or iv. inhibiting, relieving, or slowing the onset or progression of one or more symptoms of the disease or disorder.

"Therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents described herein (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

"Prophylactically effective amount" refers to an amount effective for preventing onset or initiation of a disease or condition.

"Prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

"Second therapeutic agent" refers to a therapeutic agent different from a compound of formula I and that is known to treat the disease or condition of interest. For example, the second therapeutic agent may be an agent used to treat influenza infections. In an embodiment, the second therapeutic agent is a neuraminidase inhibitor is oseltamivir, zanamivir, peramivir, or a pharmaceutically acceptable salt thereof, and any combination thereof.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a compound of structural formula (I) can be administered at the same time or sequentially in any order at different points in time as a second therapeutic agent. A present compound and the second therapeutic agent can be administered separately, in any appropriate form and by any suitable route. When a present compound and the second therapeutic agent are not administered concurrently, it is understood that they can be administered in any order to a subject in need thereof.

"Pharmaceutically acceptable" describes a material that is not biologically or otherwise undesirable, i.e., without causing an unacceptable level of undesirable biological effects or interacting in a deleterious manner.

"Pharmaceutically acceptable vehicle" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation.

"Pharmaceutically acceptable carriers" for therapeutic use are well known in the pharmaceutical art, and are described, for example, in Remington's Pharmaceutical Sciences, 18th Edition (Easton, Pennsylvania: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

"Contacting" refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, cofactor, factor, or protein on which the activity of the cell, target protein, or other biological entity itself is dependent.

Pharmaceutical Compositions

In certain aspects, described herein are pharmaceutical compositions comprising a therapeutically effective amount of one or more compounds described herein and one or more pharmaceutically acceptable diluents, preservatives, solubilizers, emulsifiers, adjuvants, excipients, or carriers. The pharmaceutical composition can be used, for example, for treating diseases or conditions characterized by allergic inflammation.

Suitable excipients for non-liquid formulations are also known to those of skill in the art. A thorough discussion of pharmaceutically acceptable excipients and salts is available in Remington's Pharmaceutical Sciences, 18th Edition (Easton, Pennsylvania: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

Yet another aspect is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be affected using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one aspect, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

The compositions of the disclosure can be formulated for aerosol administration, particularly to the respiratory tract and including intranasal administration. Such compositions are prepared according to techniques well-known in the art of pharmaceutical formulation and can be prepared as solutions in saline, employing benzyl alcohol or other suitable preservatives, absorption promoters to enhance bioavailability, and/or other conventional solubilizing or dispersing agents. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of a compound described herein will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Kits

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. In other aspects, the kits further contain instructions for use.

In a further aspect, the present disclosure also provides a pharmaceutical pack or kit comprising one or more containers filled with one or more of the ingredients of the pharmaceutical compositions described herein. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

ASPECTS

Aspect 1. A compound of formula I or a pharmaceutically acceptable salt thereof

I

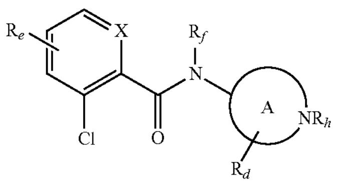

wherein

X is CH or N;

ring A is a nitrogen-containing hetercyclyl;

$R_h$ is alkyl or cycloalkyl;

$R_d$ is one to nine substituents independently selected from alkyl, halo, haloalkyl, aryl, arylalkyl and $C_3$-$C_5$ cycloalkyl;

$R_f$ is selected from H, alkyl, aryl, and arylalkyl; and $R_e$ is one to five substituents independently selected from halo, haloalkyl, aryl, arylalkyl and —$NO_2$.

Aspect 2. The compound of Aspect 1, wherein the compound has the formula II or a pharmaceutically acceptable salt thereof

II

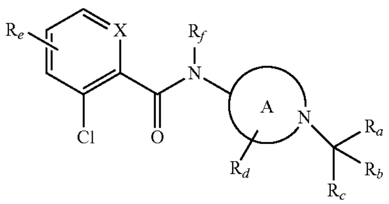

wherein

X is CH or N;

ring A is a nitrogen-containing hetercyclyl selected from tetrahyroquinolyl, indolyl, indolinyl and piperidinyl;

$R_a$, $R_b$ and $R_c$ are independently selected from H, alkyl and aryl, or any two of $R_a$, $R_b$ and $R_c$, together with the C atom to which they are attached define a cycloalkyl;

$R_d$ is one to nine substituents independently selected from alkyl, halo, haloalkyl, aryl, arylalkyl and $C_3$-$C_5$ cycloalkyl;

$R_f$ is selected from H, alkyl, aryl, and arylalkyl; and $R_e$ is one to five substituents independently selected from halo, haloalkyl, aryl, arylalkyl and —$NO_2$.

Aspect 3. The compound of Aspect 1 selected from

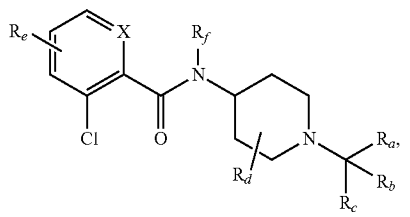

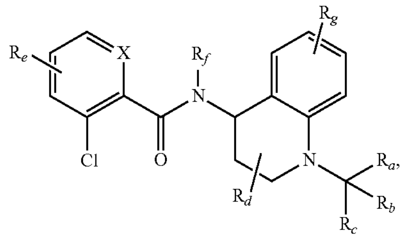

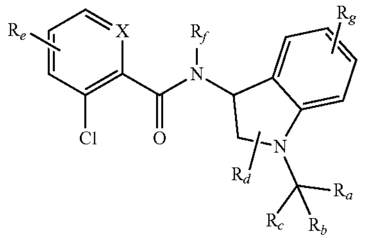

and

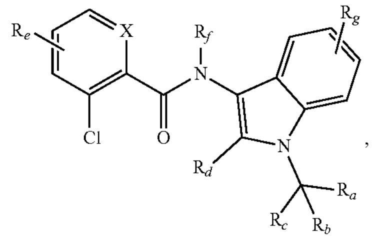

, wherein Rg is one to four substituents independently selected from halo, haloalkyl, aryl, arylalkyl and $C_3$-$C_5$ cycloalkyl, or a pharmaceutically acceptable salt thereof.

Aspect 4. The compound of any one of Aspects 1-3 or a pharmaceutically acceptable salt thereof, wherein X is CH.

Aspect 5. The compound of any one of Aspects 1-4 or a pharmaceutically acceptable salt thereof, wherein $R_f$ is H.

Aspect 6. The compound of any one of Aspects 1-5 or a pharmaceutically acceptable salt thereof, wherein $R_e$ is selected from —$NO_2$, Cl and —$CF_3$.

Aspect 7. The compound of any one of Aspects 1-6 or a pharmaceutically acceptable salt thereof, wherein Rd is selected from H and halo and Rg is selected from H, halo, haloalkyl and $C_3$-$C_5$ cycloalkyl.

Aspect 8. The compound of any one of Aspects 1-7 or a pharmaceutically acceptable salt thereof, wherein halo is F and haloalkyl is $CF_3$.

Aspect 9. The compound of Aspect 1, wherein the compound has the structure

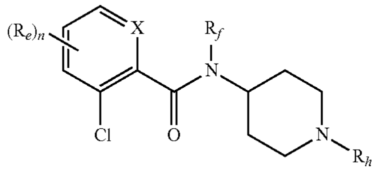

wherein $R_e$ is haloalkyl, X is CH, and n is 1 to 4.

Aspect 10. The compound of Aspect 9, wherein $R_e$ is haloalkyl, X is CH, and $R_f$ is H.

Aspect 11. The compound of Aspect 9, wherein $R_e$ is haloalkyl, X is CH, $R_f$ is H, and $R_h$ is an alkyl group.

Aspect 12. The compound of any one of Aspects 9-11, wherein n is 1.

Aspect 13. The compound of any one of Aspects 9-12, wherein $R_e$ is $CF_3$.

Aspect 14. The compound of any one of Aspects 9-13, wherein $R_e$ is at the 4 position of the aryl ring.

Aspect 15. The compound of any one of Aspects 9-14, wherein $R_h$ is a tert-butyl group or an isopropyl group.

Aspect 16. The compound of Aspect 1 selected from

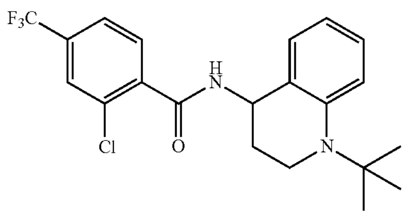

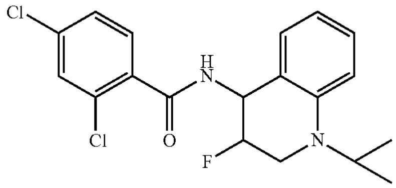

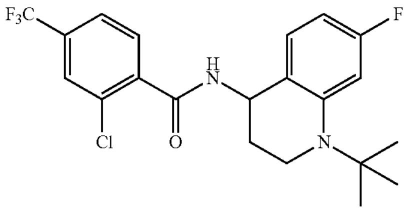

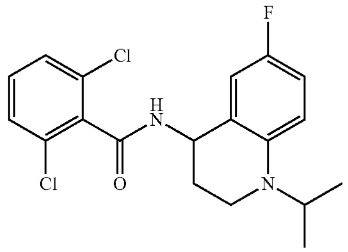

-continued
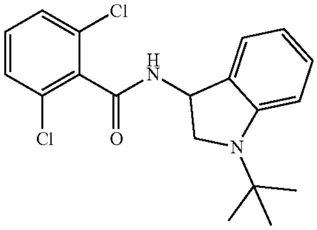
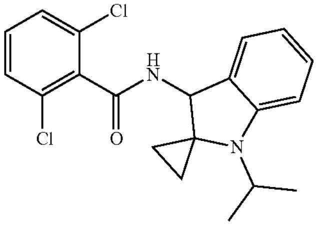
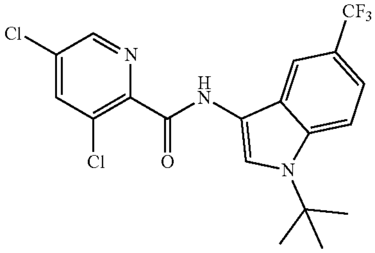
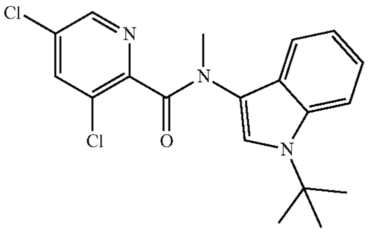
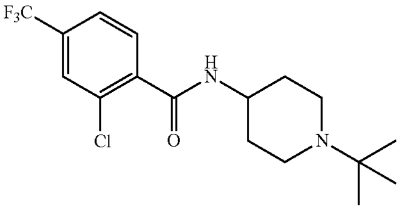
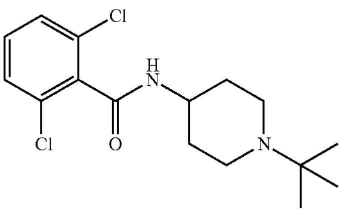
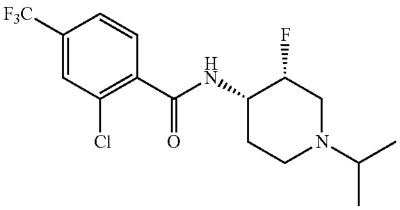
-continued
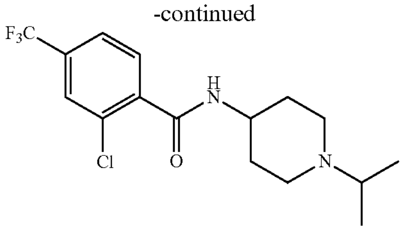
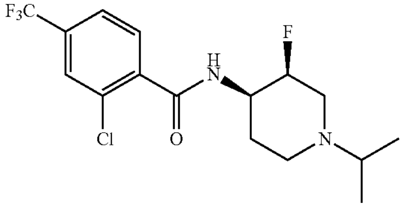
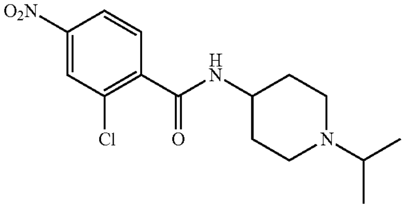
or a pharmaceutically acceptable salt thereof.
Aspect 17. The compound according to Aspect 1 selected from
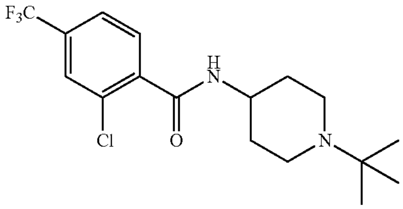
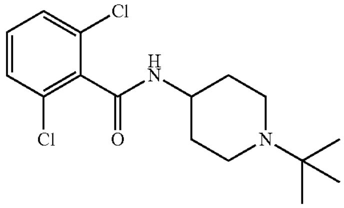
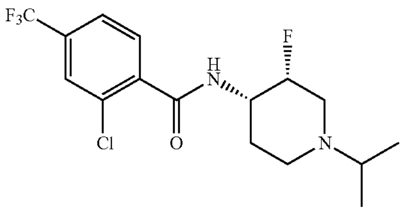
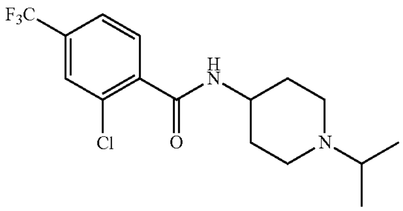

-continued

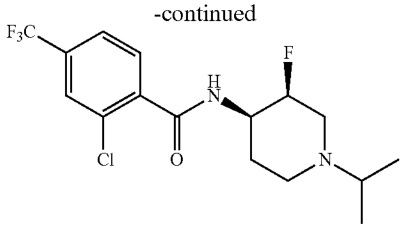

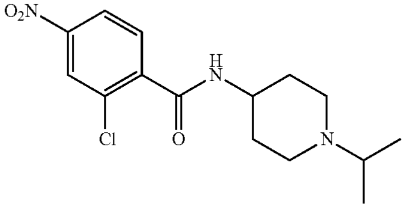

or a pharmaceutically acceptable salt thereof.

Aspect 18. A composition comprising a compound of any one of Aspects 1-17 and a pharmaceutically acceptable excipient.

Aspect 19. A method of treating an influenza infection in a subject comprising administering to the subject a compound of any one of Aspects 1-17.

Aspect 20. The method of Aspect 19 further comprising administering to the subject a neuraminidase inhibitor.

Aspect 21. The method of Aspect 20, wherein the neuraminidase inhibitor comprises oseltamivir, zanamivir, peramivir, or a pharmaceutically acceptable salt thereof.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the product purity and yield obtained from the described process. Only reasonable and routine experimentation will be required to optimize such process conditions.

Compounds

Compounds described herein may be prepared as shown in Scheme 1, where we used the Schotten-Baumann reaction to produce the desired benzoylated amines. In Scheme 1, the synthesis of compound 1 is shown as an example, prepared from 2,6-dichlorobenzoyl chloride (35) and 4-amino-l-isopropylpiperidine (36).

Scheme 1

Synthesis of acylated 4-aminopiperidines (as shown for hit compound 1).

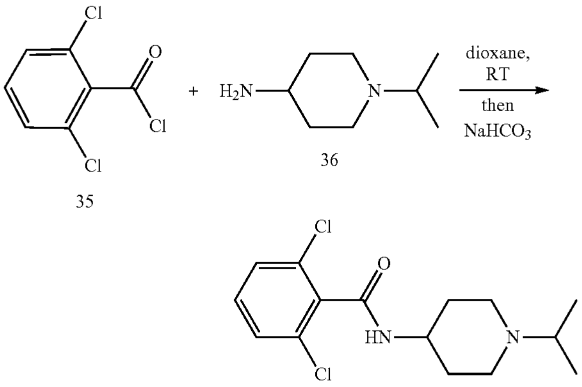

35 36

1

To develop SAR in the series of compounds related to hit compound 1, we have synthesized 33 new analogs using the chemistry described in Scheme 1. A rapid HIV pseudotyped virus assay was employed to evaluate all new compounds, as it is a reliable surrogate assay for flu entry with alleviated safety concerns.[35-38]

For those compounds that showed greater than 80% inhibition at a concentration of 12.5 μM in the $H_5N_1$ pseudotype VSV in A549 cells, dose-response studies were conducted to determine $EC_{50}$ values. Compounds with varied substituents on the aromatic ring, and with the inclusion of a heteroatom in the aromatic ring are shown in Table 1.

TABLE 1

Chemical structures and anti-influenza activity of compounds 1-8.

| No. | ID code | 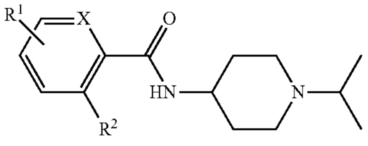 | $H_5N_1$ pseudotype assay[a] % inhibition at 12.5 μM | $EC_{50}$ (μM) |
|---|---|---|---|---|
| 1 | ING-14-5 | X = CH, $R^1$ = 6-Cl, $R^2$ = Cl | 90 | 3.04 ± 1.13 |
| 2 | ING-14-4 | X = CH, $R^1$ = 6-$CF_3$, $R^2$ = Cl | 85 | 5.62 ± 2.16 |
| 3 | ING-14-27 | X = CH, $R^1$ = H, $R^2$ = $CF_3$ | 31 | — |
| 4 | ING-14-37 | X = CH, $R^1$ = 4-$NO_2$, $R^2$ = Cl | 97 | 0.72 ± 0.09 |
| 5 | ING-14-33 | X = CH, $R^1$ = 4-$CF_3$, $R^2$ = Cl | 99 | 0.36 ± 0.05 |
| 6 | ING-14-36 | X = N, $R^1$ = 4-Cl, $R^2$ = Cl | 39 | — |

TABLE 1-continued

Chemical structures and anti-influenza activity of compounds 1-8.

| No. | ID code | 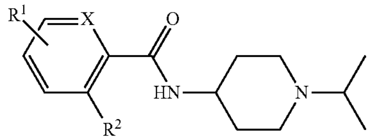 | $H_5N_1$ pseudotype assay[a] % inhibition at 12.5 μM | $EC_{50}$ (μM) |
|---|---|---|---|---|
| 7 | ING-14-43 | X = N, $R^1$ = 4-$CF_3$, $R^2$ = Cl | 76 | — |
| 8 | ING-14-44 | X = N, $R^1$ = H, $R^2$ = Cl | 40 | — |

[a]Dose-response studies were conducted to determine $EC_{50}$ values for those compounds that showed more than 80% inhibition at 12.5 μM concentration, $EC_{50}$ values were calculated by four-parameter dose-response curve-fitting in GraphPad Prism. Results are from three replicates. Percent inhibition errors are estimated to be <10%; $EC_{50}$ data are presented as mean ± SD.

In Table 2 are shown variations in three parts of the molecule, e.g., the aromatic ring, the amide, and the piperidine N-substituent. Interestingly, compound 9, which contains an N-methyl group on the amide nitrogen, was still active ($EC_{50}$=4.45 μM), while introduction of a bulky benzyl group as in compound 10 resulted in reduced potency (only 67% inhibition) compared with the parent hit compound. These data lead us to believe that the amide NH group might not be involved in a critical hydrogen-bonding interaction with the receptor, but perhaps the ratio of amide rotamers is important for receptor binding, and the N-benzyl group changes the ratio of amide rotamers to provide a less favorable mix.

TABLE 2

Chemical structures and anti-influenza activity of compounds 9-19.

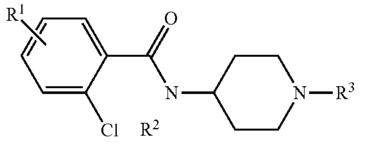

1-18

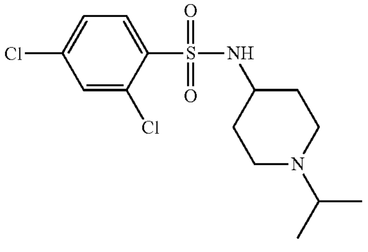 [SMILES: CC(C)N1CCC(NS(=O)(=O)c2ccc(Cl)cc2Cl)CC1]

| N | ID code | 19 | $H_5N_1$ pseudotype assay[a] % inhibition at 12.5 μM | $EC_{50}$ (μM) |
|---|---|---|---|---|
| 9 | ING-14-24 | $R^1$ = 6-Cl, $R^2$ = Me, $R^3$ = i-Pr | 91 | 4.45 ± 0.92 |
| 10 | ING-14-57 | $R^1$ = 6-Cl, $R^2$ = Bn, $R^3$ = i-Pr | 64 | — |
| 11 | ING-14-29 | $R^1$ = 6-Cl, $R^2$ = H, $R^3$ = cyclo-Pr | 33 | — |
| 12 | ING-14-30 | $R^1$ = 6-Cl, $R^2$ = H, $R^3$ = cyclo-Bu | 76 | — |
| 13 | ING-14-45 | $R^1$ = 6-Cl, $R^2$ = H, $R^3$ = t-Bu | 99 | 0.51 ± 0.04 |
| 14 | ING-14-46 | $R^1$ = 6-Cl, $R^2$ = H, $R^3$ = i-Bu | 89 | 2.15 ± 0.64 |
| 15 | ING-14-42 | $R^1$ = 6-Cl, $R^2$ = H, $R^3$ = oxetan-3-yl | 7 | — |
| 16 | ING-14-66 | $R^1$ = 4-$CF_3$, $R^2$ = H, $R^3$ = t-Bu | 99 | 0.24 ± 0.09 |
| 17 | ING-14-67 | $R^1$ = 4-$CF_3$, $R^2$ = H, $R^3$ = i-Bu | 73 | — |
| 18 | ING-14-65 | $R^1$ = 4-$CF_3$, $R^2$ = H, $R^3$ = cyclohexyl | 98 | 0.91 ± 0.25 |
| 19 | ING-14-3 | | 1 | — |

[a]Dose-response studies were conducted to determine $EC_{50}$ values for those compounds that showed more than 80% inhibition at 12.5 μM concentration, $EC_{50}$ values were calculated by four-parameter dose-response curve-fitting in GraphPad Prism. Results are from three replicates. Percent inhibition errors are estimated to be <10%; $EC_{50}$ data are presented as mean ± SD.

The results of many variations on the piperidine portion of the molecule, where the 2,6-dichloro derivative, 9, (91% inhibition at 12.5 μM; $H_5N_1$ pseudotype assay) serves as the parent hit compound, are shown in Table 3.

TABLE 3

Chemical structures and anti-influenza activity of compounds 20-26.

| N | ID code | 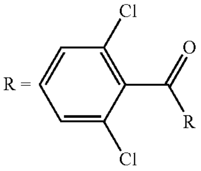 | $H_5N_1$ pseudotype assay % inhibition at 12.5 uM[a] |
|---|---|---|---|
| 20 | ING-14-18 | 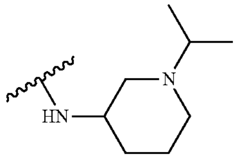 [SMILES: *NC1CCCN(C(C)C)C1] | 14 |
| 21 | ING-14-28 | 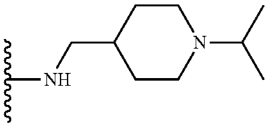 [SMILES: *NCC1CCN(C(C)C)CC1] | 23 |
| 22 | ING-14-31 | 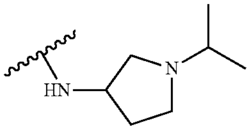 [SMILES: *NC1CCN(C(C)C)C1] | 11 |

TABLE 3-continued

Chemical structures and anti-influenza activity of compounds 20-26.

| N | ID code | 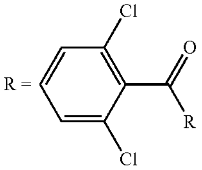 | $H_5N_1$ pseudotype assay % inhibition at 12.5 uM[a] |
|---|---|---|---|
| 23 | ING-14-15 | 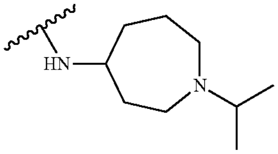 [SMILES: *NC1CCCN(C(C)C)CC1] | 71 |
| 24 | ING-14-54 | 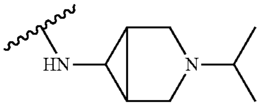 [SMILES: *NC1C2CN(C(C)C)CC21] | 61 |
| 25 | ING-14-12 | 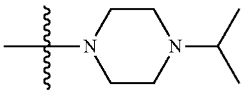 | 4 |
| 26 | ING-14-19 | 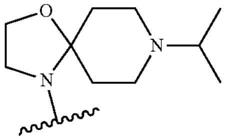 [SMILES: *N1CCOC12CCN(C(C)C)CC2] | 19 |

Results are from three replicates.
Percent inhibition errors are estimated to be <10%

Compounds described herein having a methyl group or one or two fluorine atoms to the 3-position of the piperidine ring are shown in Table 4.

TABLE 4

Chemical structures and anti-influenza activity of compounds 27-34.

| N | ID code | 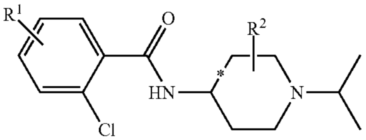 | $H_5N_1$ pseudotype assay % inhibition at 12.5 uM | $H_5N_1$ pseudotype assay $EC_{50}$ (μM) |
|---|---|---|---|---|
| 27 | ING-14-49 | *4-R,S, $R^1$ = 6-Cl, $R^2$ = 4-Me | 75 | — |
| 28 | ING-14-56 | *4-R, $R^1$ = 6-Cl, $R^2$ = 3-(S)—Me | 64 | — |
| 29 | ING-14-53 | *4-S, $R^1$ = 6-Cl, $R^2$ = 3-(S)—F | 87 | 1.81 ± 0.45 |
| 30 | ING-14-55 | *4-R,S, $R^1$ = 6-Cl, $R^2$ = 3,3-di-F | 77 | — |
| 31 | ING-14-70 | *4-S, $R^1$ = 4-$CF_3$, $R^2$ = 3-(S)—F | 93 | 1.16 ± 0.67 |
| 32 | ING-14-73 | *4-S, $R^1$ = 4-$CF_3$, $R^2$ = 3-(R)—F | 99 | 0.63 ± 0.48 |
| 33 | ING-14-71 | *4-R, $R^1$ = 4-$CF_3$, $R^2$ = 3-(R)—F | 87 | 2.93 ± 0.30 |
| 34 | ING-14-72 | *4-R, $R^1$ = 4-$CF_3$, $R^2$ = 3-(S)—F | 99 | 0.67 ± 0.20 |

[a] Dose-response studies were conducted to determine $EC_{50}$ values for those compounds that showed more than 80% inhibition at 12.5 μM concentration, $EC_{50}$ values were calculated by four-parameter dose-response curve-fitting in GraphPad Prism. Results are from three replicates. Percent inhibition errors are estimated to be <10%; $EC_{50}$ data are presented as mean ± SD.

The fourteen most potent inhibitors, including the original hit, 1, were evaluated in the secondary assay where MDCK cells were infected with 0.01 MOI of a reporter virus, PR8-PB2-Gluc, carrying a Gaussia luciferase gene in the influenza A/Puerto Rico/8/1934 (PR8) $H_1N_1$ virus background. For antiviral treatment, infected cells were cultured in the presence of increasing concentrations of test compound. To determine the cytotoxicity of the compounds, MDCK cell viability was assessed at 48 hours. All tested compounds show inhibitory effect against IAV replication, with $EC_{50}$s ranging from 72 to 989 nM (Table 5). No cytotoxicity was detected at the highest dose of 100 µM for all compounds. The best compound to emerge from both assays is ING-14-66 (compound 16), with an $EC_{50}$ value of 72 nM (Table 5).

TABLE 5

Antiviral activity of selected acylated 4-aminopiperidines in the infectious IAV.

| N | ID code | $EC_{50}$ (nM) |
|---|---|---|
| 1 | ING-14-5 | 272 ± 37 |
| 2 | ING-14-4 | 587 ± 140 |
| 4 | ING-14-37 | 211 ± 43 |
| 5 | ING-14-33 | 380 ± 182 |
| 9 | ING-14-24 | 724 ± 36 |
| 13 | ING-14-45 | 113 ± 18 |
| 14 | ING-14-46 | 852 ± 79 |
| 16 | ING-14-66 | 72 ± 24 |
| 18 | ING-14-65 | 505 ± 174 |
| 29 | ING-14-53 | 885 ± 50 |
| 31 | ING-14-70 | 324 ± 105 |
| 32 | ING-14-73 | 263 ± 33 |
| 33 | ING-14-71 | 989 ± 323 |
| 34 | ING-14-72 | 195 ± 49 |
| Oseltamivir carboxylate | | 181 ± 69 |

[a] $EC_{50}$ values were calculated by four-parameter dose-response curve-fitting in GraphPad. Results are from three replicates; data are presented as mean ± SD.

To validate the new acylated 4-aminopiperidines as inhibitors of influenza A, four of the most potent inhibitors (Table 5) were evaluated compared to the hit, 1, in the infectious assay where influenza virus $H_1N_1$ (A/Puerto Rico/8/1934) or $H_5N_1$ (A/Vietnam/1203/2004) strains were used to infect A549 cells. Strikingly, there was a significant decrease in viral titer of both $H_1N_1$ and $H_5N_1$ upon treatment with inhibitors as compared to DMSO control. Thus, these data are consistent with the pseudovirus assay results and corroborate the potential inhibitory effects of these acylated 4-aminopiperidines on influenza virus replication. Furthermore, our preliminary data revealed that these acylated 4-aminopiperidines act as potent inhibitors of the oseltamivir resistant influenza A (HiNi) virus strain with the most common H274Y resistance mutation. In the virus reduction assay, these compounds completely inhibited virus replication at the 20 µM screening concentration, while oseltamivir carboxylate, used as a control, had no inhibitory effect.

It was hypothesized that a combination of antiviral agents with different modes of action, such as the NA inhibitor oseltamivir and our novel HA fusion inhibitors, could result in synergistic antiviral activity. In in vitro combination studies, MDCK cells were infected with 0.01 MOI of PR8-NS1-Gluc and treated with varied doses of OC alone, ING-14-66 (compound 16)alone or OC and ING-14-66 in combination. To assess the synergistic activity of the drug combination, the concentration for OC was set to be twice lower than the $EC_{50}$ value for the drug as a single agent. The drug concentration needed to cause 30%, 40%, 50%, 60%, 70%, 80%, and 90% reductions in luciferase levels ($IC_{30-90}$) were determined and used to calculate Combination Index (CI) values. Compound 1 and OC demonstrated synergistic inhibitory effects against the PR8-NS1-Gluc virus quantitatively evaluated by the median effect plot method[39] (Table 6). As shown in Table 6, individually administered doses of oseltamivir and ING-14-66 were not as effective in preventing the infectivity, as when applied in combination. The lowest value of CI (0.34) was achieved with the treatment with OC and ING-14-66 used at 156 and 114 nM, respectively, leading to a 90% reduction in viral replication. These preliminary results demonstrate the beneficial effect of combination therapy with these drugs that inhibit viral replication through different mechanisms at different stages of the viral life cycle, and their potential effectiveness in clinical therapy.

TABLE 6

Synergistic anti-influenza activity of oseltamivir carboxylate (OC) and ING-14-66.

| Compound | $EC_{30}$ (nM) | $EC_{40}$ (nM) | $EC_{50}$ (nM) | $EC_{60}$ (nM) | $EC_{70}$ (nM) | $EC_{80}$ (nM) | $EC_{90}$ (nM) |
|---|---|---|---|---|---|---|---|
| OC | 160 | 229 | 318 | 441 | 629 | 972 | 1871 |
| ING-14-66 | 134 | 160 | 187 | 219 | 260 | 321 | 439 |
| ING-14-66 with 156 nM OC | 35 | 42 | 49 | 57 | 68 | 83 | 114 |
| CI* | 1.23 | 0.94 | 0.75 | 0.61 | 0.51 | 0.42 | 0.34 |

*CI values of <1, =1, and >1 indicate synergism, additive effect, and antagonism, respectively[39]

Based on its superior potency in the infectious strain, we prioritized compound 16 for hepatic metabolic stability testing in liver microsomes (LM). The percentages of compound remaining after 60 minutes of incubation in both mouse and human LM in the presence of NADPH oxidase were 94% and 97%, respectively, indicating excellent metabolic stability.

Pharmacokinetic analysis of the plasma and liver levels of ING-14-66 in BALB/c mice following i.p. administration or gavage (p.o.) indicated that the maximal levels are rapidly reached, with $T_{max}$=30 min (Table 7). The Cmax level in the plasma with the 10 mg/kg i.p. dose was found to be 1136 ng/ml or 3.12 μM, whereas at 5x the dose p.o., Cmax was 7× higher at 7641 ng/mL, indicating excellent oral bioavailability.

TABLE 7

Pharmacokinetic parameters of ING-14-66.

| | | i.p. (10 mg/kg) | | p.o. (50 mg/kg) | |
|---|---|---|---|---|---|
| Parameter | Unit | Plasma | Liver | Plasma | Liver |
| $T_{1/2}$ | h | 1.53 | 2.47 | 2.16 | 2.58 |
| $T_{max}$ | h | 0.5 | 0.25 | 0.5 | 1.0 |
| $C_{max}$ | ng/g | 1136 | 24900 | 7641 | 70400 |
| $AUC_{(0\text{-}8\ h)}$ | ng · h/g | 3282 | 66400 | 23705 | 292000 |

$T_{1/2}$, terminal half-life; $C_{max}$, the maximum concentration that a drug achieves after dosing; AUC, area under curve. The blood and liver samples were collected at 0.033, 0.25, 0.5, 1, 2, 4, 6 and 8 h, with three mice in each group.

Compound 16 (ING-14-66) was also tested against CYP3A4 and CYP2C9, the two most common human CYP isoforms in drug metabolism and was found to have $IC_{50}$ values>100 μM, suggesting that this compound is unlikely to interfere with the metabolism of other xenobiotics or endogenous compounds in the phase I hepatic metabolism pathway.

Experimental

General. All solvents were purchased from commercial suppliers and used without further purification. $^1H$ and $^{13}C$ NMR spectra were recorded on Bruker DPX-400 or AVANCE-400 spectrometer, at 400 MHz and 100 MHz respectively. NMR chemical shifts were reported in δ (ppm) using residual solvent peaks as standard ($CDCl_3$: 7.26 ppm ($^1H$), 77.23 ppm ($^{13}C$); $CD_3OD$: 3.31 ppm ($^1H$), 49.15 ppm ($^{13}C$); DMSO-d6: 2.50 ppm ($^1H$), 39.52 ppm ($^{13}C$)). Mass spectra were measured in the ESI mode at an ionization potential of 70 eV with an LC-MS MSD (Hewlett-Packard). Purity of all final compounds (greater than 95%) was determined by analytical HPLC (ACE 3AQ $C_8$ column (150×4.6 mm, particle size 3 μM) with detection at 254 and 280 nm on a Shimadzu SPD-20A VP detector; flow rate=1.0 mL/min; gradient of 10-95% acetonitrile in water (both containing 0.1 vol % of FA) in 20 min.

General Method A. Coupling of amines with acyl chloride derivatives. To a solution of amine (1 eq) in dry dioxane (2 mL/mmol) appropriately substituted acyl chloride (1 eq) was added and the reaction mixture was stirred at room temperature under argon for 3-12 hours until completion as monitored by TLC. The precipitated salt was separated, washed with EtOAc (2×5 ml) and treated with a mixture of DCM and $NaHCO_3$ (aq), the organic phase was collected, washed with water and brine, and dried over $Na_2SO_4$. Solvent was removed under vacuum to provide crude product, which was further purified by flash chromatography (CombiFlash) eluting with methanol in dichloromethane 5-30% to yield the desired product. Preparative thin-layer chromatography with 5% methanol in dichloromethane was used for additional purification of analytical sample when needed.

General Method B. Boc deprotection. tert-Butyl-carboxylate was treated with 4N HCl in dioxane (10 mL/mmol). The reaction was stirred overnight at room temperature, then the volatiles were removed under vacuum and the residue was treated with 2M NaOH (aq). The aqueous phase was extracted with DCM (2×30 ml), the combined organic layers were washed with brine, dried over $Na_2SO_4$, filtered and concentrated under vacuum. The product was used in next step without purification.

General Method C. Reductive amination. To a solution of amine (1 eq), acetone (7 eq), and acetic acid (0.5 eq) in THF (2 mL/mmol) sodium triacetoxyborohydride (2 eq) was added and the reaction mixture was stirred at room temperature for 24 h. The solvent was evaporated and the residue was dissolved in EtOAc (20 mL), washed with $NaHCO_3$, brine, dried over $Na_2SO_4$, filtered and concentrated under vacuum. Crude product was purified by Preparative thin-layer chromatography using 5% methanol in dichloromethane.

2,6-Dichloro-N-(1-isopropylpiperidin-4-yl)benzamide (ING-14-5) (1). General Method A was used to synthesize this compound. Yield: 212 mg, 96%. HPLC purity: 98%. $^1$HNMR (400 MHz, DMSO-$d_6$) δ0.94 (d, J=6.6 Hz, 6H), 1.39-1.48 (m, 2H), 1.79-1.82 (m, 2H), 2.18 (t, J=9.7 Hz, 2H), 2.65 (quintet, J=6.6 Hz, 1H), 2.73-2.76 (m, 2H), 3.68-3.74 (m, 1H), 7.39-7.53 (m, 3H), 8.53 (d, J=7.9 Hz, 1H). $^{13}C$ NMR (100 MHz, $CDCl_3$) δ18.3, 32.1, 47.3, 47.4, 54.4, 127.9, 130.4, 132.1, 136.0, 163.6. HRMS (ESI) calculated for $C_{15}H_{21}C_{12}N2O$ ($[M+H]^+$): 315.1031, found: 315.1036.

2-Chloro-N-(1-isopropylpiperidin-4-yl)-6-(trifluoromethyl)benzamide (ING-14-4) (2). General Method A was used to synthesize this compound. Yield: 30 mg, 28%. HPLC purity: 96.7%. $^1H$ NMR (400 MHz, $CDCl_3$) δ1.03 (d, J=6.5 Hz, 6H), 1.52-1.59 (m, 2H), 2.06-2.09 (m, 2H), 2.31-2.34 (m, 2H), 2.72-2.86 (m, 4H), 4.30 (m, 1H), 5.77 (bs, 1H), 7.40-7.58 (m, 3H). $^{13}C$ NMR (100 MHz, $CDCl_3$) δ18.3, 31.9, 47.3, 47.4, 54.5, 121.5, 124.2, 124.54, 124.59, 128.9, 129.2, 130.0, 132.8, 133.2, 134.8, 163.5. HRMS (ESI) calculated for $C_{16}H_{21}ClF_3N_2O$ ($[M+H]^+$): 349.1295, found: 349.1256.

N-(1-Isopropylpiperidin-4-yl)-2-(trifluoromethyl)benzamide (ING-14-27) (3). General Method A was used to synthesize this compound. Yield: 370 mg, 83%. HPLC purity: 98%. $^1H$ NMR (400 MHz, DMSO-d6) δ1.05 (d, J=6.5 Hz, 6H), 1.52-1.55 (m, 2H), 2.07-2.09 (m, 2H), 2.29-2.35 (m, 2H), 2.75 (quintet, J=6.5 Hz, 1H), 2.85-2.88 (m, 2H), 4.00-4.025 (m, 1H), 5.63 (d, J=6.4 Hz, 1H), 7.51-7.70 (m, 4H). $^{13}C$ NMR (100 MHz, DMSO-d6) δ18.0, 31.8, 47.0, 47.1, 54.1, 125.8, 128.3, 129.3, 131.6, 166.6. HRMS (ESI) calculated for $C_{16}H_{22}F_3N_2O$ ($[M+H]^+$): 315.1684, found: 315.1685.

2-Chloro-N-(1-isopropylpiperidin-4-yl)-4-nitrobenzamide (ING-14-37) (4). General Method A was used to synthesize this compound. Yield: 90 mg, 39%. HPLC purity: 93%. $^1H$ NMR (400 MHz, $CDCl_3$) δ1.03 (d, J=6.6 Hz, 6H), 1.57-1.63 (m, 2H), 2.02-2.06 (m, 2H), 2.32 (dt, J=2.2, 11.5 Hz, 2H), 2.76 (quintet, J=6.5 Hz, 1H), 2.84-2.87 (m, 2H), 3.95 (m, 1H), 6.32 (d, J=7.9 Hz, 1H), 7.62 (d, J=8.5 Hz, 1H), 8.07 (dd, J=2.2, 8.5 Hz, 1H), 8.18 (d, J=2.2 Hz, 1H). $^{13}C$ NMR (100 MHz, $CDCl_3$) δ18.2, 32.0, 47.2, 47.8, 54.6, 121.9, 125.1, 130.5, 131.9, 141.2, 148.5, 164.0. HRMS (ESI) calculated for $C_{15}H_{21}C_1N_3O_3$ ([M+H]$^+$): 326.1271, found: 326.1263.

2-Chloro-N-(1-isopropylpiperidin-4-yl)-4-(trifluoromethyl) benzamide (ING-14-33) (5). General Method A was used to synthesize this compound. Yield: 11.6 mg, 4.7% (two steps). HPLC purity: 96%. $^1$H NMR (400 MHz, $CDCl_3$) δ1.07 (d, J=6.5 Hz, 6H), 1.58-1.65 (m, 2H), 2.09-2.13 (m, 2H), 2.36 (dt, J=2.2, 11.5 Hz, 2H), 2.76 (quintet, J=6.5 Hz, 1H), 2.80-2.87 (m, 2H), 4.03-4.05 (m, 1H), 6.02 (d, J=7.7 Hz, 1H), 7.59 (dd, J=0.9, 8.0 Hz, 1H), 7.69 (d, J=0.9 Hz, 1H), 7.76 (d, J=8.0 Hz, 1H). $^{13}$C NMR (100 MHz, $CDCl_3$) δ18.3, 32.3, 47.3, 47.7, 54.5, 124.0, 127.3, 130.6, 131.2, 138.6, 164.5. HRMS (ESI) calculated for $C_{16}H_{21}ClF_3N_2O$ ([M+H]$^+$): 349.1295, found: 349.1289.

3,5-Dichloro-N-(1-isopropylpiperidin-4-yl)picolinamide (ING-14-36) (6). General Method A was used to synthesize this compound. Yield: 15 mg, 2.8% (two steps) HPLC purity: 96%. $^1$H NMR (400 MHz, $CDCl_3$) δ1.25 (d, J=5.4 Hz, 6H), 1.61-1.67 (m, 2H), 2.04-2.07 (m, 2H), 2.35 (dt, J=0.9, 11.3 Hz, 2H), 2.78 (quintet, J=6.5 Hz, 1H), 2.89-3.36 (m, 2H), 3.92-3.97 (m, 1H), 7.56 (d, J=7.7 Hz, 1H), 7.84 (d, J=2.1 Hz, 1H), 8.41 (d, J=2.1 Hz, 1H). $^{13}$C NMR (100 MHz, $CDCl_3$) δ18.3, 32.2, 47.0, 47.4, 54.6, 132.2, 134.0, 139.5, 144.4, 145.0, 161.9. HRMS (ESI) calculated for $C_{14}H_{20}C_{12}N_3O$ ([M+H]$^+$): 316.0983, found: 316.0975.

3-Chloro-N-(1-isopropylpiperidin-4-yl)-5-(trifluoromethyl)picolinamide (ING-14-43) (7). General Method A was used to synthesize this compound. Yield: 60 mg, 83%. HPLC purity: 99%.

$^1$H NMR (400 MHz, $CDCl_3$) δ1.04 (d, J=6.5 Hz, 6H), 1.56-1.65 (m, 2H), 2.03-2.07 (m, 2H), 2.33 (dt, J32 2.3, 11.6 Hz, 2H), 2.75 (quintet, J=6.5 Hz, 1H), 2.86-2.89 (m, 2H), 3.95 (m, 1H), 7.57 (d, J=7.9 Hz, 1H), 8.04 (d, J=1.1 Hz, 1H), 8.70 (d, J=1.1 Hz, 1H). $^{13}$C NMR (100 MHz, $CDCl_3$) δ18.3, 32.3, 47.2, 47.4, 54.5, 118.0, 120.8, 123.5, 126.2, 128.5, 128.8, 129.2, 129.5, 132.0, 137.5, 137.53, 142.7, 142.8, 149.5, 161.5. HRMS (ESI) calculated for $C_{15}H_{20}ClF_3N_3O$ ([M+H]$^+$): 350.1247, found: 350.1238.

3-Chloro-N-(1-isopropylpiperidin-4-yl)picolinamide (ING-14-44) (8). General Method A was used to synthesize this compound. Yield: 62 mg, 77%. HPLC purity: 99%. 1H NMR (400 MHz, $CDCl_3$) δ1.02 (d, J=6.5 Hz, 9H), 1.57-1.63 (m, 2H), 2.00-2.04 (m, 2H), 2.30 (dt, J=2.4, 11.6 Hz, 2H), 2.73 (quintet, J=6.5 Hz, 1H), 2.83-2.86 (m, 2H), 3.91-3.93 (m, 1H), 7.28 (dd, J=4.5, 8.2 Hz, 1H), 7.65 (d, J=7.8 Hz, 1H), 7.76 (dd, J=1.5, 8.2 Hz, 1H), 8.41 (dd, J=1.5, 4.5 Hz, 1H). $^{13}$C NMR (100 MHz, $CDCl_3$) δ18.3, 32.2, 46.9, 47.5, 54.5, 126.2, 131.7, 140.2, 146.0, 146.5, 162.7. HRMS (ESI) calculated for $C_{14}H_{21}ClN_3O$ ([M+H]$^+$): 282.1373, found: 282.1373.

2,6-Dichloro-N-(1-isopropylpiperidin-4-yl)-N-methylbenzamide (ING-14-24) (9). General Method A was used to synthesize this compound. Yield: 30 mg, 28%. HPLC purity: 98%. $^1$H NMR (400 MHz, $CDCl_3$) δ1.05 (d, J=6.5 Hz, 6H), 1.80-1.88 (m, 4H), 2.31-2.37 (m, 2H), 2.72 (s, 3H), 2.72-2.89 (m, 1H), 2.96-2.99 (m, 2H), 4.62-4.70 (m, 1H), 7.21-7.34 (m, 3H). $^{13}$C NMR (100 MHz, $CDCl_3$) δ18.0, 28.4, 29.4, 47.5, 50.7, 54.0, 127.6, 129.6, 131.0, 135.6, 164.8. HRMS (ESI) calculated for $C_{16}H_{23}C_{12}N_2O$ ([M+H]$^+$): 329.1187, found: 329.1182.

N-Benzyl-2,6-dichloro-N-(1-isopropylpiperidin-4-yl)benzamide (ING-14-57) (10). General Method A was used to synthesize this compound. Yield: 61 mg, 42%. HPLC purity: 95%. $^1$H NMR (400 MHz, $CDCl_3$) δ0.92 (d, J=6.5 Hz, 6H), 1.73-1.90 (m, 6H), 2.58-2.63 (m, 1H), 2.79-2.82 (m, 2H), 3.23-3.43 (m, 1H), 4.83 (s, 2H), 7.22-7.38 (m, 6H), 7.48 (d, J=7.2 Hz, 2H). $^{13}$C NMR (100 MHz, $CDCl_3$) δ18.3, 31.4, 45.0, 48.2, 54.2, 59.0, 126.8, 127.5, 128.2, 128.3, 130.1, 135.8, 138.8, 165.9. HRMS (ESI) calculated for $C_{22}H_{27}Cl_2N_2O$ ([M+H]$^+$): 405.1500, found: 405.1496.

2,6-Dichloro-N-(1-cyclopropylpiperidin-4-yl)benzamide (ING-14-29) (11). General Method A was used to synthesize this compound. Yield: 392 mg, 70%. HPLC purity: 97.6%. $^1$H NMR (400 MHz, $CDCl_3$) δ0.37-0.48 (m, 4H), 1.4-1.56 (m, 2H), 1.59-1.62 (m, 2H), 2.05-2.08 (m, 2H), 2.37 (t, J=10.1 Hz, 2H), 2.97-3.00 (m, 2H), 4.03-4.11 (m, 1H), 5.68 (d, J=7.5 Hz, 1H), 7.21-7.35 (m, 3H). $^{13}$C NMR (100 MHz, $CDCl_3$) δ5.6, 31.4, 38.0, 46.9, 51.9, 127.6, 130.1, 131.8, 135.6, 163.3. HRMS (ESI) calculated for $C_{15}H_{19}Cl_2N_2O$ ([M+H]$^+$): 313.0874, found: 313.0873.

2,6-Dichloro-N-(1-cyclobutylpiperidin-4-yl)benzamide (ING-14-30) (12). General Method A was used to synthesize this compound. Yield: 262 mg, 49%. HPLC purity: 98.5%. $^1$H NMR (400 MHz, $CDCl_3$) δ1.51-1.56 (m, 2H), 1.66-1.69 (m, 2H), 1.82-2.39 (m, 8H), 2.70 (quintet, J=7.9 Hz, 1H), 2.78-2.81 (m, 2H), 4.00-4.07 (m, 1H), 5.74 (d, J=7.8 Hz, 1H), 7.20-7.32 (m, 3H). $^{13}$C NMR (100 MHz, $CDCl_3$) δ13.7, 27.0, 31.0, 46.7, 47.9, 59.8, 127.6, 130.1, 131.8, 135.6, 163.3. HRMS (ESI) calculated for $C_{16}H_{21}Cl_2N_2O$ ([M+H]$^+$): 327.1031, found: 327.1029.

N-(1-(tert-Butyl)piperidin-4-yl)-2,6-dichlorobenzamide (ING-14-45) (13). General Method A was used to synthesize this compound. Yield: 10 mg, 8%. HPLC purity: 97%. $^1$H NMR (400 MHz, $CDCl_3$) δ1.10 (s, 6H), 1.54-1.63 (m, 2H), 2.10-2.14 (m, 2H), 2.34 (dt, J=2.0, 11.6 Hz, 2H), 3.01-3.04 (m, 2H), 4.02-4.06 (m, 1H), 5.67 (d, J=7.6 Hz, 1H), 7.23-7.32 (m, 3H). $^{13}$C NMR (100 MHz, $CDCl_3$) δ26.1, 32.5, 44.7, 47.4, 54.2, 128.0, 130.5, 132.2, 136.1, 163.7. HRMS (ESI) calculated for $C_{16}H_{23}C_{12}N_2O$ ([M+H]$^+$): 329.1187, found: 329.1194.

2,6-Dichloro-N-(1-isobutylpiperidin-4-yl)benzamide (ING-14-46) (14). General Method A was used to synthesize this compound. Yield: 61 mg, 52%. HPLC purity: 98%. $^1$H NMR (400 MHz, $CDCl_3$) δ0.88 (d, J=6.4 Hz, 6H), 1.52-1.65 (m, 2H), 1.74 (quintet, J=6.8 Hz, 1H), 2.01-2.12 (m, 6H), 2.77-2.80 (m, 2H), 4.00-4.03 (m, 1H), 5.82 (d, J=5.0 Hz, 1H), 7.20-7.29 (m, 3H). $^{13}$C NMR (100 MHz, $CDCl_3$) δ20.9, 25.7, 31.8, 47.3, 52.5, 66.8, 127.9, 130.4, 132.2, 136.1, 163.6. HRMS (ESI) calculated for $C_{16}H_{23}Cl_2N_2O$ ([M+H]$^+$): 329.1187, found: 329.1190.

2,6-Dichloro-N-(1-(oxetan-3-yl)piperidin-4-yl)benzamide (ING-14-42) (15). General Method A was used to synthesize this compound. Yield: 35 mg, 33%. HPLC purity: 97.7%. $^1$H NMR (400 MHz, $CDCl_3$) δ1.54-1.64 (m, 2H), 2.05 (t, J=11.5 Hz, 2H), 2.06-2.11 (m, 2H), 2.68-2.70 (m, 2H), 3.44 (quintet, J=6.4 Hz, 1H), 4.03-4.07 (m, 1H), 4.55 (t, J=6.2 Hz, 2H), 4.62 (t, J=6.2 Hz, 2H), 7.22-7.31 (m, 3H). $^{13}$C NMR (100 MHz, $CDCl_3$) δ 31.3, 46.9, 48.7, 59.1, 75.8, 128.0, 130.5, 132.2, 136.0, 163.7. HRMS (ESI) calculated for $C_{15}H_{19}C_{12}N_2O_2$ ([M+H]$^+$): 329.0824, found: 329.0811.

N-(1-(tert-Butyl)piperidin-4-yl)-2-chloro-4-(trifluoromethyl)benzamide (ING-14-66) (16).

General Method A was used to synthesize this compound. Yield: 89 mg, 59%. HPLC purity: 99%. $^1$H NMR (400 MHz, $CDCl_3$) δ1.08 (s, 9H), 1.52-1.62 (m, 1H), 2.03-2.06 (m, 2H), 2.28 (t, J=11.1 Hz, 2H), 2.98-3.01 (m, 2H), 3.95-3.97 (m, 1H), 6.27 (d, J=7.7 Hz, 1H), 7.51 (d, J=8.0 Hz, 1H), 7.62 (s, 1H), 7.66 (d, J=8.0 Hz, 1H). $^{13}$C NMR (100 MHz, $CDCl_3$) δ26.0, 32.5, 44.7, 47.6, 54.2, 121.4, 123.8, 123.9, 124.1, 127.1, 130.4, 131.2, 132.9, 133.2, 138.7, 164.6. HRMS (ESI) calculated for $C_{17}H_{23}ClF_3N_2O$ ([M+H]$^+$): 363.1451, found: 363.1451.

2-Chloro-N-(1-isobutylpiperidin-4-yl)-4-(trifluoromethyl)benzamide (ING-14-67) (17). General Method A was used to synthesize this compound. Yield: 37 mg, 25%. HPLC purity: 99%. 1 H NMR (400 MHz, $CDCl_3$) δ0.90 (d, J=6.6 Hz, 6H), 1.60-1.68 (m, 2H), 1.77-1.83 (m, 1H), 2.02-2.06 (m, 2H), 2.11-2.18 (m, 4H), 2.82-2.85 (m, 2H), 4.03 (m, 1H), 6.16 (d, J=7.7 Hz, 1H), 7.56 (dd, J=0.9, 8.0 Hz, 1H), 7.66 (d, J=0.9 Hz, 1H), 7.71 (d, J=8.0 Hz, 1H). $^{13}C$ NMR (100 MHz, $CDCl_3$) δ20.9, 25.6, 31.8, 47.5, 52.5, 66.7, 121.4, 124.0, 124.2, 127.21, 127.25, 130.5, 131.3, 133.0, 133.3, 138.7, 164.6. HRMS (ESI) calculated for $C_{17}H_{23}ClF_3N_2O$ ($[M+H]^+$): 363.1451, found: 363.1446.

2-Chloro-N-(1-cyclohexylpiperidin-4-yl)-4-(trifluoromethyl)benzamide (ING-14-65) (18). General Method A was used to synthesize this compound. Yield: 76 mg, 47%. HPLC purity: 99%. $^1H$ NMR (400 MHz, $CDCl_3$) δ1.08-1.27 (m, 5H), 1.57-1.66 (m, 3H), 1.80-1.88 (m, 4H), 2.06-2.10 (m, 2H), 2.32-2.37 (m, 1H), 2.40 (dt, J=2.3, 11.4 Hz, 2H), 2.90 (d, J=11.4 Hz, 2H), 4.01 (m, 1H), 6.15 (d, J=7.9 Hz, 1H), 7.55 (dd, J=0.9, 8.0 Hz, 1H), 7.66 (d, J=0.9 Hz, 1H), 7.70 (d, J=8.0 Hz, 1H). $^{13}C$ NMR (100 MHz, $CDCl_3$) δ25.9, 26.2, 28.7, 32.2, 47.7, 63.8, 121.4, 123.9, 124.2, 127.21, 127.24, 130.5, 131.3, 133.0, 133.3, 138.7, 164.6. HRMS (ESI) calculated for $C_{19}H_{25}ClF_3N_2O$ ($[M+H]^+$): 389.1608, found: 389.1605.

2,4-Dichloro-N-(1-isopropylpiperidin-4-yl)benzenesulfonamide (ING-14-3) (19). General Method A was used to synthesize this compound. Yield: 220 mg, 89%. HPLC purity: 99%. $^1H$ NMR (400 MHz, DMSO-d6) δ0.87 (d, J=6.5 Hz, 6H), 1.36-1.45 (m, 2H), 1.52-1.54 (m, 2H), 1.97 (t, J=11.1 Hz, 2H), 93 (m, 1H), 7.61 (dd, J=2.0, 8.5 Hz, 1H), 7.85 (d, J=2.0 Hz, 1H), 7.97 (d, J=8.5 Hz, 1H), 8.02 (d, J=6.4 Hz, 1H). $^{13}C$ NMR (100 MHz, $CDCl_3$) δ18.2, 33.0, 46.9, 51.5, 54.3, 127.5, 131.3, 131.8, 132.3, 137.2, 139.2. HRMS (ESI) calculated for $C_{14}H_{21}Cl_2N_2O_2S$ ($[M+H]^+$): 351.0701, found: 315.0676.

2,6-Dichloro-N-(1-isopropylpiperidin-3-yl)benzamide (ING-14-18) (20). General Methods A-C were used to synthesize this compound. Yield: 44 mg, 21%. HPLC purity: 98%. $^1H$ NMR (400 MHz, $CDCl_3$) δ1.05 (t, J=6.6 Hz, 6H), 1.57-1.61 (m, 2H), 1.73-1.88 (m, 2H), 2.32 (t, J=9.6 Hz, 1H), 2.50 (d, J=9.6 Hz, 1H), 2.65-2.73 (m, 3H), 4.36 (bs, 1H), 6.65 (bs, 1H), 7.24-7.31 (m, 3H). $^{13}C$ NMR (100 MHz, $CDCl_3$) δ17.2, 18.5, 22.0, 29.1, 45.2, 49.5, 2.4, 54.6, 127.9, 130.3, 132.2, 136.3, 163.2. HRMS (ESI) calculated for $C_{15}H_{21}C_{12}N_2O$ ($[M+H]^+$): 315.1031, found: 315.1027.

2,6-Dichloro-N-((1-isopropylpiperidin-4-yl)methyl)benzamide (ING-14-28) (21). General Method A was used to synthesize this compound. Yield: 293 mg, 55%. HPLC purity: 96%. $^1H$ NMR (400 MHz, $CDCl_3$) δ1.05 (d, J=6.5 Hz, 6H), 1.30-1.38 (m, 2H), 1.67-1.73 (m, 2H), 1.82-1.85 (m, 2H), 2.73 (quintet, J=6.6 Hz, 1H), 2.86-2.93 (m, 2H), 3.38 (t, J=6.4 Hz, 2H), 5.83 (bs, 1H), 7.23-7.36 (m, 5H). $^{13}C$ NMR (100 MHz, $CDCl_3$) δ17.9, 29.9, 35.6, 45.2, 48.0, 54.2, 127.6, 130.1, 131.8, 135.8, 164.1. HRMS (ESI) calculated for $C_{16}H_{23}C_{12}N_2O$ ($[M+H]^+$): 329.1187, found: 329.1192.

2,6-Dichloro-N-(1-isopropylpyrrolidin-3-yl)benzamide (ING-14-31) (22). General Method A was used to synthesize this compound. Yield: 170 mg, 72%. HPLC purity: 99%. $^1H$ NMR (400 MHz, $CDCl_3$) δ1.08 (d, J=2.8 Hz, 3H), 1.10 (d, J=2.8 Hz, 3H), 1.81 (m, 1H), 2.32-2.42 (m, 3H), 2.63 (dd, J=6.2, 9.9 Hz, 1H), 2.86 (dd, J=1.8, 9.9 Hz, 1H), 2.98 (m, 1H), 4.66-4.71 (m, 1H), 6.31 (d, J=5.9 Hz, 1H), 7.22-7.33 (m, 3H). $^{13}C$ NMR (100 MHz, $CDCl_3$) δ21.13, 21.18, 31.5, 48.6, 49.9, 54.1, 57.8, 127.6, 130.1, 131.8, 135.5, 163.2. HRMS (ESI) calculated for $C_{14}H_{19}Cl_2N_2O$ ($[M+H]^+$): 301.0874, found: 301.0868.

2,6-Dichloro-N-(1-isopropylazepan-4-yl)benzamide (ING-14-15) (23) General Methods A-C were used to synthesize this compound. Yield: 12.8 mg, 11%. HPLC purity: 98%. $^1H$ NMR (400 MHz, $CDCl_3$) δ0.95 (dd, J=1.0, 6.5 Hz, 6H), 1.70-1.73 (m, 2H), 1.93-2.04 (m, 3H), 2.47-2.51 (m, 1H), 2.65-2.69 (m, 1H), 2.76-2.90 (m, 4H), 4.55-4.61 (m, 1H), 7.18-7.32 (m, 4H). $^{13}C$ NMR (100 MHz, $CDCl_3$) δ17.4, 24.8, 31.7, 32.6, 45.9, 47.1, 50.0, 55.3, 127.5, 129.8, 131.7, 162.9. HRMS (ESI) calculated for $C_{15}H_{21}Cl_2N_2O$ ($[M+H]^+$): 329.1187, found: 329.1174.

2, 6-Dichloro-N-(3-isopropyl-3-azabicyclo[3. 1.0] hexan-6-yl)benzamide (ING-14-54) (24). General Method A was used to synthesize this compound. Yield: 32 mg, 21%. HPLC purity: 97%. (diastereomers) $^1H$ NMR (400 MHz, $CDCl_3$) δ0.89 (d, J=6.4 Hz, 6H), 1.02 (d, J=6.4 Hz, 6H), 1.60 (m, 2H), 1.68 (m, 2H), 2.25-2.27 (m, 3H), 2.39-2.47 (m, 3H), 2.67 (d, J=9.0 Hz, 2H), 2.78 (s, 1H), 3.16 (s, 1H), 3.20 (d, J=9.0 Hz, 2H), 5.8 (s, 1H), 6.16 (s, 1H), 7.20-7.31 (m, 3H), 720-7.38 (m, 3H). $^{13}C$ NMR (100 MHz, $CDCl_3$) δ21.2, 21.5, 24.3, 25.0, 30.5, 31.6, 51.7, 52.0, 53.7, 127.9, 130.4, 130.5, 131.4, 132.3, 136.0, 165.3. HRMS (ESI) calculated for $C_{15}H_{19}Cl_2N_2O$ ($[M+H]^+$): 313.0874, found: 313.0870.

(2,6-Dichlorophenyl)-(4-isopropylpiperazin-1-yl)methanone (ING-14-12) (25). General Method A was used to synthesize this compound. Yield: 366 mg, 78%. HPLC purity: 99%. $^1H$ NMR (400 MHz, $CDCl_3$) δ1.04 (d, J=6.5 Hz, 6H), 2.51 (t, J=5.0 Hz, 2H), 2.62 (t, J=5.0 Hz, 2H), 2.74 (quintet, J=7.5 Hz, 1H), 3.25 (t, J=5.0 Hz, 2H), 3.85 (t, J=5.0 Hz, 2H), 7.26-7.34 (m, 3H). $^{13}C$ NMR (100 MHz, $CDCl_3$) δ18.3, 41.8, 46.5, 48.0, 48.8, 54.5, 128.0, 130.2, 131.7, 135.1, 163.6. HRMS (ESI) calculated for $C_{14}H_{19}C_{12}N_2O$ ($[M+H]^+$): 301.0874, found: 301.0869.

(2,6-Dichlorophenyl)-(8-isopropyl-1-oxa-4,8-diazaspiro[4.5]decan-4-yl)methanone (ING-14-19) 26). General Methods A-C were used to synthesize this compound. Yield: 64 mg, 41%. HPLC purity: 98%. $^1H$ NMR (400 MHz, $CDCl_3$) δ1.03 (d, J=6.5 Hz, 6H), 1.63 (d, J=12.2 Hz, 2H), 2.47 (t, J=11.2 Hz, 2H), 2.79-2.82 (m, 3H), 2.93-3.00 (m, 2H), 3.31 (t, J=6.2 Hz, 2H), 3.97 (t, J=6.2 Hz, 1H), 7.2-7.31 (m, 3H). $^{13}C$ NMR (100 MHz, $CDCl_3$) δ18.4, 31.8, 45.3, 36.6, 53.8, 63.1, 95.0, 128.0, 130.2, 131.0, 136.5, 161.3. HRMS (ESI) calculated for $C_{17}H_{23}Cl_2N_2O_2$ ($[M+H]^+$): 357.1137, found: 357.1128.

2,6-Dichloro-N-(1-isopropyl-4-methylpiperidin-4-yl)benzamide (ING-14-49) (27). General Method A was used to synthesize this compound. Yield: 68 mg, 51%. HPLC purity: 98%. $^1H$ NMR (400 MHz, $CDCl_3$) δ1.46 (s, 6H), 1.52-1.62 (m, 5H), 2.02-2.18 (m, 2H), 3.16-3.22 (m, 2H), 3.74-3.77 (m, 2H), 5.61 (s, 1H), 7.21-7.21 (m, 3H). $^{13}C$ NMR (100 MHz, $CDCl_3$) δ25.9, 28.0, 36.0, 53.3, 79.6, 128.0, 130.4, 132.1, 136.5, 154.7, 164.0. HRMS (ESI) calculated for $C_{16}H_{23}Cl_2N_2O$ ($[M+H]^+$): 331.1158, found: 331.0571.

2,6-Dichloro-N-((3S,4R)-1-isopropyl-3-methoxypiperidin-4-yl)benzamide (ING-14-56) (28). General Method A was used to synthesize this compound. Yield: 71 mg, 19%. HPLC purity: 95%. $^1H$ NMR (400 MHz, $CDCl_3$) δ0.99 (d, J=6.5 Hz, 3H), 2.05 (d, J=6.5 Hz, 3H), 1.87-1.95 (m, 2H), 2.21-2.24 (m, 1H), 2.37 (dt, J=3.1, 8.0 Hz, 1H), 2.75-2.82 (m, 2H), 3.04-3.07 (m, 1H), 3.38 (s, 3H), 3.50 (m, 1H), 4.20-4.22 (m, 1H), 6.18 (d, J=8.0 Hz, 1H), 7.22-7.31 (m, 3H). $^{13}C$ NMR (100 MHz, $CDCl_3$) δ16.8, 19.2, 27.6, 47.2, 47.8, 49.0, 54.2, 56.3, 128.0, 130.5, 132.2, 136.1, 163.8. HRMS (ESI) calculated for $C_{16}H_{23}Cl_2N_2O_2$ ($[M+H]^+$): 345.1137, found: 345.1128.

2,6-Dichloro-N-((3S,45)-3-fluoro-1-isopropylpiperidin-4-yl)benzamide (ING-14-53) (29). General Method A was used to synthesize this compound. Yield: 158 mg, 41%. HPLC purity: 99%. (diastereomers)$^1$H NMR (400 MHz, $CDCl_3$) δ1.00 (d, J=6.3 Hz, 3H), 1.02 (d, J=6.3 Hz, 3H), 1.50-1.53 (m, 2H), 2.21-2.33 (m, 6H), 2.71-2.80 (m, 4H), 3.09-3.14 (m, 2H), 4.05-4.06 (m, 2H), 4.32 (m, 1H), 4.45 (m, 1H), 6.17-6.19 (m, 2H), 7.18-7.27 (m, 6H). $^{13}$C NMR (100 MHz, $CDCl_3$) δ17.9, 18.4, 29.7, 29.8, 46.8, 51.5, 51.8, 52.2, 52.4, 54.1, 89.2, 91.0, 127.9, 130.5, 132.2, 135.8, 164.3. HRMS (ESI) calculated for $C_{15}H_{20}Cl_2FN_2O$ ([M+H]$^+$): 333.0937, found: 333.0933.

2,6-Dichloro-N-(3,3-difluoro-1-isopropylpiperidin-4-yl) benzamide (ING-14-55) (30). General Method A was used to synthesize this compound. Yield: 178 mg, 47%. HPLC purity: 97.5%. $^1$H NMR (400 MHz, $CDCl_3$) δ1.05 (s, 6H), 1.72-1.74 (m, 1H), 2.16 (m, 1H), 2.35-2.54 (m, 2H), 2.88 (m, 2H), 3.15 (m, 1H), 4.41 (m, 1H), 6.09 (d, J=6.3 Hz, 1H), 7.25-7.30 (m, 3H). $^{13}$C NMR (100 MHz, $CDCl_3$) δδ17.5, 18.5, 29.4, 29.49, 47.0, 50.8, 51.02, 51.22, 53.1, 53.3, 53.4, 53.6, 53.8, 116.4, 118.8, 121.3, 128.0, 130.8, 132.2, 135.5, 164.3. HRMS (ESI) calculated for $C_{15}H_{19}Cl_2F_2N_2O$ ([M+H]$^+$): 351.0843, found: 383.1123.

2-Chloro-N-((3S,45)-3-fluoro-1-isopropylpiperidin-4-yl)-4-(trifluoromethyl)benzamide (ING-14-70) (31). General Method A was used to synthesize this compound. Yield: 54 mg, 18%. HPLC purity: 99%. $^1$H NMR (400 MHz, $CDCl_3$) δ1.05 (d, J=4.0 Hz, 3H), 1.07 (d, J=4.0 Hz, 3H), 1.56-1.60 (m, 1H), 2.25-2.39 (m, 3H), 2.80-2.87 (m, 2H), 3.20-3.23 (m, 1H), 4.10-4.19 (m, 1H), 4.41-4.54 (m, 1H), 6.34 (d, J=7.7 Hz, 1H), 7.56 (d, J=8.0 Hz, 1H), 7.67(s, 1H), 7.73 (d, J=8.0 Hz, 1H). $^{13}$C NMR (100 MHz, $CDCl_3$) δ17.9, 18.3, 29.,9, 30.0, 46.9, 51.5, 51.7, 52.6, 52.8, 54.3, 89.5, 91.3, 121.4, 124.0, 124.1, 127.2, 130.6, 131.3, 133.1, 133.5, 138.4, 165.5. HRMS (ESI) calculated for $C_{16}H_{20}ClF_3N_2O$ ([M+H]$^+$): 367.1200, found: 367.1195.

2-Chloro-N-((3R,4R)-3-fluoro-1-isopropylpiperidin-4-yl)-4-(trifluoromethyl)benzamide (ING-14-71) (32). General Method A was used to synthesize this compound. Yield: 70 mg, 23%. HPLC purity: 98.8%. $^1$H NMR (400 MHz, $CDCl_3$) δ1.05 (d, J=4.0 Hz, 3H), 1.07 (d, J=4.0 Hz, 3H), 1.56-1.60 (m, 1H), 2.25-2.39 (m, 3H), 2.80-2.87 (m, 2H), 3.20-3.23 (m, 1H), 4.10-4.19 (m, 1H), 4.41-4.54 (m, 1H), 6.34 (d, J=7.7 Hz, 1H), 7.56 (d, J=8.0 Hz, 1H), 7.67(s, 1H), 7.73 (d, J=8.0 Hz, 1H). $^{13}$C NMR (100 MHz, $CDCl_3$) δ17.9, 18.3, 29.,9, 30.0, 46.9, 51.5, 51.7, 52.6, 52.8, 54.3, 89.5, 91.3, 121.4, 124.0, 124.1, 127.2, 130.6, 131.3, 133.1, 133.5, 138.4, 165.5. HRMS (ESI) calculated for $C_{16}H_{20}ClF_3N_2O$ ([M+H]$^+$): 367.1200, found: 367.1199.

2-Chloro-N-((3S,4R)-3-fluoro-1-isopropylpiperidin-4-yl)-4-(trifluoromethyl)benzamide (ING-14-72) (33). General Method A was used to synthesize this compound. Yield: 81 mg, 48%. HPLC purity: 99%. $^1$H NMR (400 MHz, $CDCl_3$) δ1.05 (d, J=5.5 Hz, 3H), 1.06 (d, J=5.5 Hz, 3H), 1.92-1.98 (m, 2H), 2.34-2.54 (m, 2H), 2.84 (quintet, J=6.6 Hz, 1H), 2.92-2.95 (m, 1H), 4.16-4.28 (m, 1H), 4.78 (d, J=13.0 Hz, 1H), 6.51 (d, J=8.5 Hz, 1H), 7.57 (d, J=8.0 Hz, 1H), 7.67 (s, 1H), 7.72 (d, J=8.0 Hz, 1H). $^{13}$C NMR (100 MHz, $CDCl_3$) δ17.6, 18.2, 27.3, 47.1, 49.3, 49.5, 50.8, 51.0, 54.0, 87.5, 89.3, 121.4, 123.9, 124.0, 124.1, 127.31, 127.35, 130.5, 131.4, 133.2, 133.5, 138.2, 164.8 HRMS (ESI) calculated for $C_{16}H_{20}ClF_3N_2O$ ([M+H]$^+$): 367.1200, found: 367.1199.

2-Chloro-N-((3R,45)-3-fluoro-1-isopropylpiperidin-4-yl)-4-(trifluoromethyl)benzamide (ING-14-73) (34). General Method A was used to synthesize this compound. Yield: 146 mg, 48%. HPLC purity: 99%. $^1$H NMR (400 MHz, $CDCl_3$) δ1.05 (d, J=5.5 Hz, 3H), 1.06 (d, J=5.5 Hz, 3H), 1.92-1.98 (m, 2H), 2.34-2.54 (m, 2H), 2.84 (quintet, J=6.6 Hz, 1H), 2.92-2.95 (m, 1H), 4.16-4.28 (m, 1H), 4.78 (d, J=13.0 Hz, 1H), 6.51 (d, J=8.5 Hz, 1H), 7.57 (d, J=8.0 Hz, 1H), 7.67 (s, 1H), 7.72 (d, J=8.0 Hz, 1H). $^{13}$C NMR (100 MHz, $CDCl_3$) δ17.6, 18.2, 27.3, 47.1, 49.3, 49.5, 50.8, 51.0, 54.0, 87.5, 89.3, 121.4, 123.9, 124.0, 124.1, 127.31, 127.35, 130.5, 131.4, 133.2, 133.5, 138.2, 164.8 HRMS (ESI) calculated for $C_{16}H_{20}ClF_3N_2O$ ([M+H]$^+$): 367.1200, found: 367.1201.

Cell-based protocol to identify entry inhibitors using a pseudotype virus. Low-passage A549 cells were infected with influenza A virus (HA of $H_5N_1$, Goose/Qinghai/59/05) following a previously published protocol[32] in the presence and absence of compounds at 12.5 μM. Plates were incubated for 48 h and the infection was then quantified by the luciferase activity of the infected A549 cells using the Neolite Reporter Gene Assay System (Perkin Elmer; Boston, Mass.). Compounds that showed≥80% inhibition at 12.5 μM concentration were further evaluated to determine their $EC_{50}$ values using four-parameter logistic regression analysis in GraphPad Prism (Graphpad Software; San Diego, Calif.).

Influenza A reporter PR8-PB2-Gluc virus and PR8-NS1-Gluc virus protocol. Madin-Darby canine kidney (MDCK) epithelial cells were grown in Dulbecco's modified Eagle's medium (DMEM; Cellgro, Manassas, Va., USA) supplemented with 10% fetal bovine serum (FBS; Gibco, Carlsbad, Calif., USA), 1000 units/mL penicillin, and 100 μg/mL of streptomycin (Invitrogen, Carlsbad, Calif., USA). Infections were performed in Opti-MEM containing 2 μg/mL N-tosyl-L-phenylalanine chloromethyl ketone (TPCK)-trypsin (Sigma-Aldrich, St. Louis, Mo., USA). All cells were cultured at 37° C. in 5% $CO_2$. The influenza A reporter PR8-PB2-Gluc virus and PR8-NS1-Gluc virus were generated and stocked as previously described.[40]

Antiviral determination. Antiviral evaluation was performed using reporter PR8-PB2-Gluc virus as previously described.[41] Briefly, MDCK cells grown in 96-well plates were infected with IAV PR8-PB2-Gluc at an MOI of 0.01 $TCID_{50}$/cell, in absence or presence of increasing concentrations of test compound. After 1 h incubation at 37° C., the inoculums were removed and cells were washed with PBS. Fresh Opti-MEM containing 2 μg/ml TPCK-trypsin were added for culture. 36 hours later, the cells were lysed and subjected to luciferase assay using Pierce Guassia luciferase glow assay kit (Thermo scientific, Rockford, Ill., USA) according to the manufacturer's instructions. For antiviral treatment, infected cells were cultured in presence of increasing concentrations of test compound. To determine the toxicity of the compounds, MDCK cells grown in 96-well plates were treated with increasing concentrations of test compound, and the cell viability were detected 48 hours later.

Combinational studies with oseltamivir carboxylate. MDCK cells growing in 24 well plates were infected by PR8-NS1-Gluc at an MOI of 0.01. After 1 h incubation at 37° C., cells were washed and treated with serial concentrations of compounds alone or in combination. At 48-hr post infection, the virus replication was monitored by luciferase assay using BioLux Gaussia Luciferase Assay Kit (NEB, Ipswich, Mass., USA) as previously described.[42] Data were analyzed according to the method of Chou-Talalay[39]. The $EC_{30}$, $EC_{40}$, $EC_{50}$, $EC_{60}$, $EC_{70}$, $EC_{80}$ and $EC_{90}$ values (i.e., the drug concentration needed to cause 30%, 40%, 50%, 60%, 70%, 80%, and 90% reductions in luciferase level) were chosen for comparison. Combination index (CI) values were calculated using the formula: CI=CA,x/ECx,A+CB,x/ECx,B where CA,x and CB,x are the concentrations of compounds used in combination to achieve x % drug effect. ECx,A and ECx,B are the concentrations for single agent to achieve the same effect. The combination effect was determined acscording to the following criteria: CI<1.0, synergy; CI=1.0, additive; CI>1.0, antagonism.

Infectious virus replication inhibition assay. Influenza virus $H_1N_1$ (A/Puerto Rico/8/1934) or $H_5N_1$ (A/Vietnam/1203/2004; Low pathogenic) were incubated with indicated amounts of compound at room temperature for 30 min. Subsequently, the mixture was added to A549 cells seeded in 12-well plates (3×105 cells/well) a day prior to infection and incubated at 37° C. for 1 h. After that, the mixture was removed and the cells were washed with PBS to remove unbound virus. The cells were incubated with DMEM—0.2 BSA media supplemented, containing 1 μg of TPCK trypsin (Sigma). At 48 h post-infection, viral titers in the supernatants were determined by standard plaque assay in MDCK cells.

Throughout this publication, various publications are referenced. The disclosures of these publications in their entireties are hereby incorporated by reference into this application in order to more fully describe the methods, compositions, and compounds herein.

Various modification and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

REFERENCES

1. Das, K.; Aramini, J. M.; Ma, L. C.; Krug, R. M.; Arnold, E. Structures of influenza A proteins and insights into antiviral drug targets. *Nat Struct Mol Biol* 2010, 17 (5), 530-8.

2. Horimoto, T.; Kawaoka, Y. Designing vaccines for pandemic influenza. *Curr Top Microbiol Immunol* 2009, 333, 165-76.

3. Tscherne, D. M.; Garcia-Sastre, A. Virulence determinants of pandemic influenza viruses. *J Clin Invest* 2011, 121 (1), 6-13.

4. Kemble, G.; Greenberg, H. Novel generations of influenza vaccines. *Vaccine* 2003, 21 (16), 1789-95.

5. Poland, G. A. The 2009-2010 influenza pandemic: effects on pandemic and seasonal vaccine uptake and lessons learned for seasonal vaccination campaigns. *Vaccine* 2010, 28 (Suppl 4:), D3-13.

6. Moscona, A. Oseltamivir resistance—disabling our influenza defenses. *N Engl J Med* 2005, 353 (25), 2633-6.

7. Reddy, D. Responding to pandemic (H1N1) 2009 influenza: the role of oseltamivir. *J Antimicrob Chemother* 2010, 65 Suppl 2, ii35-ii40.

8. Schunemann, H. J.; Hill, S. R.; Kakad, M.; Bellamy, R.; Uyeki, T. M.; Hayden, F. G.; Yazdanpanah, Y.; Beigel, J.; Chotpitayasunondh, T.; Del Mar, C.; Farrar, J.; Tran, T. H.; Ozbay, B.; Sugaya, N.; Fukuda, K.; Shindo, N.; Stockman, L.; Vist, G. E.; Croisier, A.; Nagjdaliyev, A.; Roth, C.; Thomson, G.; Zucker, H.; Oxman, A. D. WHO Rapid Advice Guidelines for pharmacological management of sporadic human infection with avian influenza A (H5N1) virus. *Lancet Infect Dis* 2007, 7 (1), 21-31.

9. Ward, P.; Small, I.; Smith, J.; Suter, P.; Dutkowski, R. Oseltamivir (Tamiflu) and its potential for use in the event of an influenza pandemic. *J Antimicrob Chemother* 2005, 55 *Suppl* 1, i5-i21.

10. De Clercq, E. Antiviral agents active against influenza A viruses. *Nat Rev Drug Discov* 2006, 5 (12), 1015-25.

11. De Clercq, E.; Neyts, J. Avian influenza A (H5N1) infection: targets and strategies for chemotherapeutic intervention. *Trends Phannacol Sci* 2007, 28 (6), 280-5.

12. Lackenby, A.; Hungnes, 0.; Dudman, S. G.; Meijer, A.; Paget, W. J.; Hay, A. J.; Zambon, M. C. Emergence of resistance to oseltamivir among influenza A(H1N1) viruses in Europe. *Euro Surveill* 2008, 13 (5).

13. Lackenby, A.; Thompson, C. I.; Democratis, J. The potential impact of neuraminidase inhibitor resistant influenza. *Curr Opin Infect Dis* 2008, 21 (6), 626-38.

14. van der Vries, E.; van den Berg, B.; Schutten, M. Fatal oseltamivir-resistant influenza virus infection. *N Engl J Med* 2008, 359 (10), 1074-6.

15. Mehta, T.; McGrath, E.; Bheemreddy, S.; Salimnia, H.; Abdel-Haq, N.; Ang, J. Y.; Lum, L.; Chandrasekar, P.; Alangaden, G. J. Detection of oseltamivir resistance during treatment of 2009 H1N1 influenza virus infection in immunocompromised patients: utility of cycle threshold values of qualitative real-time reverse transcriptase PCR. *J Clin Microbiol* 48 (11), 4326-8.

16. Nguyen, H. T.; Sheu, T. G.; Mishin, V. P.; Klimov, A. I.; Gubareva, L. V. Assessment of pandemic and seasonal influenza A (H1N1) virus susceptibility to neuraminidase inhibitors in three enzyme activity inhibition assays. *Antimicrob Agents Chemother* 2010, 54 (9), 3671-7.

17. Sheu, T. G.; Deyde, V. M.; Garten, R. J.; Klimov, A. I.; Gubareva, L. V. Detection of antiviral resistance and genetic lineage markers in influenza B virus neuraminidase using pyrosequencing. *Antiviral Res* 2010, 85 (2), 354-60.

18. van der Vries, E.; Stelma, F. F.; Boucher, C. A. Emergence of a multidrug-resistant pandemic influenza A (H1N1) virus. *N Engl JMed* 2010, 363 (14), 1381-2.

19. Chen, L. F.; Dailey, N. J.; Rao, A. K.; Fleischauer, A. T.; Greenwald, I.; Deyde, V. M.; Moore, Z. S.; Anderson, D. J.; Duffy, J.; Gubareva, L. V.; Sexton, D. J.; Fry, A. M.; Srinivasan, A.; Wolfe, C. R. Cluster of Oseltamivir-Resistant 2009 Pandemic Influenza A (H1N1) Virus Infections on a Hospital Ward among Immunocompromised Patients—North Carolina, 2009. *J Infect Dis* 2011, 203 (6), 838-46.

20. Le, Q. M.; Kiso, M.; Someya, K.; Sakai, Y. T.; Nguyen, T. H.; Nguyen, K. H.; Pham, N. D.; Ngyen, H. H.; Yamada, S.; Muramoto, Y.; Horimoto, T.; Takada, A.; Goto, H.; Suzuki, T.; Suzuki, Y.; Kawaoka, Y. Avian flu: isolation of drug-resistant H5N1 virus. *Nature* 2005, 437 (7062), 1108.

21. Sambhara, S.; Poland, G. A. H5N1 Avian influenza: preventive and therapeutic strategies against a pandemic. *Annu Rev Med* 2010, 61, 187-98.

22. Moss, R. B.; Davey, R. T.; Steigbigel, R. T.; Fang, F. Targeting pandemic influenza: a primer on influenza antivirals and drug resistance. *J Antimicrob Chemother* 2010, 65 (6), 1086-93.

23. Shinde, V.; Bridges, C. B.; Uyeki, T. M.; Shu, B.; Balish, A.; Xu, X.; Lindstrom, S.; Gubareva, L. V.; Deyde, V.; Garten, R. J.; Harris, M.; Gerber, S.; Vagasky, S.; Smith, F.; Pascoe, N.; Martin, K.; Dufficy, D.; Ritger, K.; Conover, C.; Quinlisk, P.; Klimov, A.; Bresee, J. S.; Finelli, L. Triple-reassortant swine influenza A (H1) in humans in the United States, 2005-2009. *N Engl JMed* 2009, 360 (25), 2616-25.

24. Gamblin, S. J.; Skehel, J. J. Influenza hemagglutinin and neuraminidase membrane glycoproteins. *J Biol Chem* 2010, 285 (37), 28403-9.

25. Skehel, J. An overview of influenza haemagglutinin and neuraminidase. *Biologicals* 2009, 37 (3), 177-8.

26. Skehel, J. J.; Wiley, D. C. Receptor binding and membrane fusion in virus entry: the influenza hemagglutinin. *Annu Rev Biochem* 2000, 69, 531-69.

27. Vanderlinden, E.; Goktas, F.; Cesur, Z.; Froeyen, M.; Reed, M. L.; Russell, C. J.; Cesur, N.; Naesens, L. Novel inhibitors of influenza virus fusion: structure-activity relationship and interaction with the viral hemagglutinin. *J Virol* 2010, 84 (9), 4277-88.

28. Leneva, I. A.; Russell, R. J.; Boriskin, Y. S.; Hay, A. J. Characteristics of arbidol-resistant mutants of influenza virus: implications for the mechanism of anti-influenza action of arbidol. *Antiviral Res* 2009, 81 (2), 132-40.

29. Luo, G.; Toni, A.; Harte, W. E.; Danetz, S.; Cianci, C.; Tiley, L.; Day, S.; Mullaney, D.; Yu, K. L.; Ouellet, C.; Dextraze, P.; Meanwell, N.; Colonno, R.; Krystal, M. Molecular mechanism underlying the action of a novel fusion inhibitor of influenza A virus. *J Virol* 1997, 71 (5), 4062-70.

30. Plotch, S. J.; O'Hara, B.; Morin, J.; Palant, 0.; LaRocque, J.; Bloom, J. D.; Lang, S. A., Jr.; DiGrandi, M. J.; Bradley, M.; Nilakantan, R.; Gluzman, Y. Inhibition of influenza A virus replication by compounds interfering with the fusogenic function of the viral hemagglutinin. *J Virol* 1999, 73 (1), 140-51.

31. Russell, R. J.; Kerry, P. S.; Stevens, D. J.; Steinhauer, D. A.; Martin, S. R.; Gamblin, S. J.; Skehel, J. J. Structure of influenza hemagglutinin in complex with an inhibitor of membrane fusion. *Proc Natl Acad Sci USA* 2008, 105 (46), 17736-41.

32. Wang, J.; Cheng, H.; Ratia, K.; Varhegyi, E.; Hendrickson, W. G.; Li, J.; Rong, L. A comparative high-throughput screening protocol to identify entry inhibitors of enveloped viruses. *J Biomol Screen* 2014, 19 (1), 100-7.

33. Shah, S. K.; Chen, N.; Guthikonda, R. N.; Mills, S. G.; Malkowitz, L.; Springer, M. S.; Gould, S. L.; DeMartino, J. A.; Carella, A.; Carver, G.; Holmes, K.; Schleif, W. A.; Danzeisen, R.; Hazuda, D.; Kessler, J.; Lineberger, J.; Miller, M.; Emini, E. A.; MacCoss, M. Synthesis and evaluation of CCRS antagonists containing modified 4-piperidinyl-2-phenyl-1-(phenylsulfonylamino)-butane. *Bioorganic & Medicinal Chemistry Letters* 2005, 15 (4), 977-982.

34. Pandit, C. R.; Mani, N. S. Expedient Reductive Amination of Aldehyde Bisulfite Adducts. *Synthesis-Stuttgart* 2009, (23), 4032-4036.

35. Manicassamy, B.; Wang, J.; Jiang, H.; Rong, L. Comprehensive Analysis of Ebola Virus GP1 in Viral Entry. *J Virol* 2005, 79 (8), 4793-805.

36. Manicassamy, B.; Rong, L. Expression of Ebolavirus glycoprotein on the target cells enhances viral entry. *Virol J*2009, 6, 75.

37. Tscherne, D. M.; Manicassamy, B.; Garcia-Sastre, A. An enzymatic virus-like particle assay for sensitive detection of virus entry. *J Virol Methods* 2010, 163 (2), 336-43.

38. Guo, Y.; Rumschlag-Booms, E.; Wang, J.; Xiao, H.; Yu, J.; Wang, J.; Guo, L.; Gao, G. F.; Cao, Y.; Caffrey, M.; Rong, L. Analysis of hemagglutinin-mediated entry tropism of H5N1 avian influenza. *Virol J* 2009, 6 (1), 39.

39. Chou, T. C.; Talalay, P. Quantitative analysis of dose-effect relationships: the combined effects of multiple drugs or enzyme inhibitors. *Adv Enzyme Regul* 1984, 22, 27-55.

40. Zhao, X.; Wang, L.; Cui, Q.; Li, P.; Wang, Y.; Zhang, Y.; Yang, Y.; Rong, L.; Du, R. A Mechanism Underlying Attenuation of Recombinant Influenza A Viruses Carrying Reporter Genes. *Viruses* 2018, 10 (12).

41. Zhao, X.; Wang, Y.; Cui, Q.; Li, P.; Wang, L.; Chen, Z.; Rong, L.; Du, R. A Parallel Phenotypic Versus Target-Based Screening Strategy for RNA-Dependent RNA Polymerase Inhibitors of the Influenza A Virus. *Viruses* 2019, 11 (9).

42. Li, P.; Cui, Q.; Wang, L.; Zhao, X.; Zhang, Y.; Manicassamy, B.; Yang, Y.; Rong, L.; Du, R. A Simple and Robust Approach for Evaluation of Antivirals Using a Recombinant Influenza Virus Expressing Gaussia Luciferase. *Viruses* 2018, 10 (6).

The invention claimed is:

1. A compound is selected from the group of compounds consisting of:

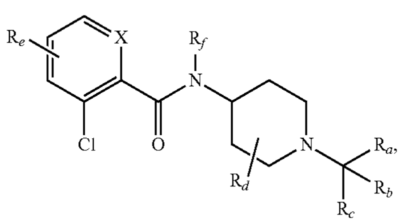

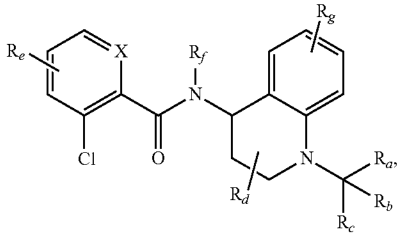

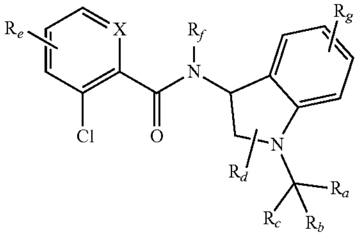

and

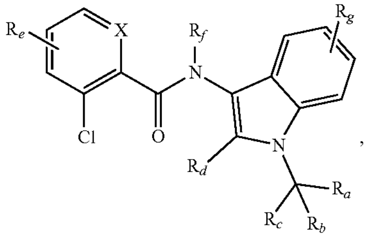

, wherein

X is CH or N;

$R_d$ is one to nine substituents independently selected from alkyl, halo, haloalkyl, aryl, arylalkyl and $C_3$-$C_5$ cycloalkyl;

$R_f$ is selected from H, alkyl, aryl, and arylalkyl;

$R_e$ is one to five substituents independently selected from halo, haloalkyl, aryl, arylalkyl and —$NO_2$;

$R_g$ is one to four substituents independently selected from halo, haloalkyl, aryl, arylalkyl and $C_3$-$C_5$ cycloalkyl, and $R_a$, $R_b$ and $R_c$ are independently selected from H, alkyl and aryl, or any two of $R_a$, $R_b$ and $R_c$, together with the C atom to which they are attached define a cycloalkyl, or a pharmaceutically acceptable salt thereof.

2. The compound of claim 1 or a pharmaceutically acceptable salt thereof, wherein X is CH.

3. The compound of claim 2 or a pharmaceutically acceptable salt thereof, wherein $R_f$ is H or Me.

4. The compound of claim 3 or a pharmaceutically acceptable salt thereof, wherein $R_e$ is selected from $—NO_2$, Cl and $—CF_3$.

5. The compound of claim 4 or a pharmaceutically acceptable salt thereof, wherein $R_d$ is selected from H and halo and $R_g$ is selected from H, halo, haloalkyl and $C_3$-$C_5$ cycloalkyl.

6. The compound of claim 5 or a pharmaceutically acceptable salt thereof, wherein halo is F and haloalkyl is $CF_3$.

7. A compound of formula II or a pharmaceutically acceptable salt thereof

II

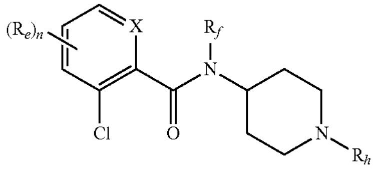

wherein $R_h$ is alkyl or cycloalkyl; and $R_e$ is haloalkyl, X is CH, and n is 1 to 4, and $R_f$ is H or Me.

8. The compound of claim 7, wherein $R_e$ is haloalkyl, X is $R_h$ is an alkyl group.

9. The compound of claim 7, wherein n is 1.

10. The compound of claim 7, wherein $R_e$ is $CF_3$.

11. The compound of claim 7, wherein $R_e$ is at the 4-position of the aryl ring, para to the carbonyl group.

12. The compound of claim 7, wherein $R_h$ is a tert-butyl group or an isopropyl group.

13. A compound selected from the group of compounds consisting of:

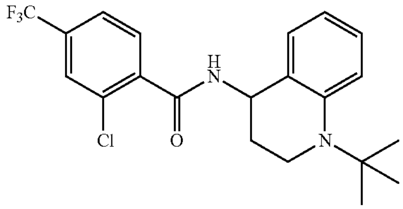

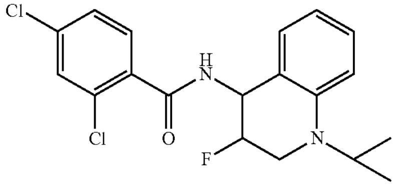

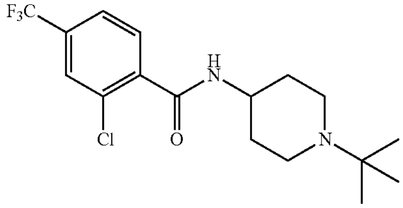

-continued

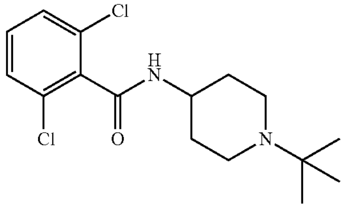

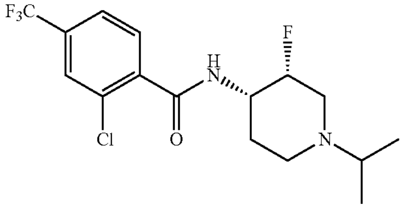

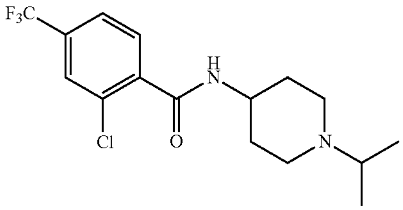

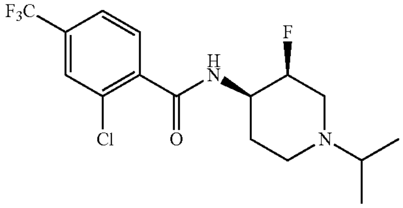

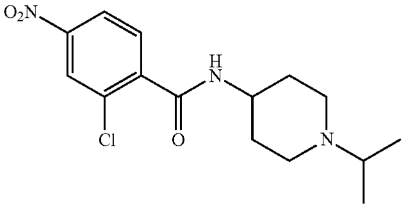

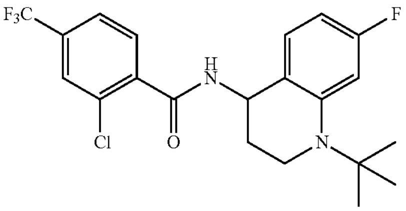

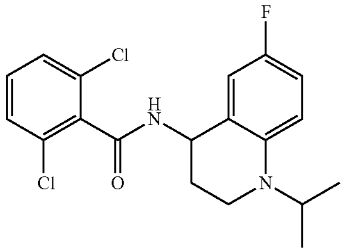

-continued

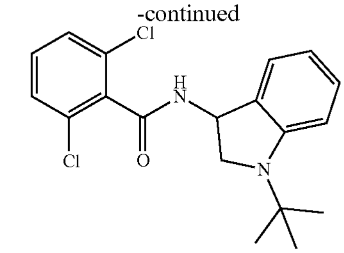

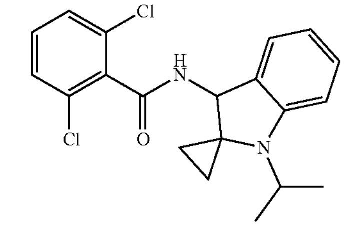

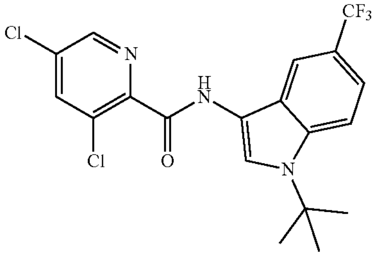

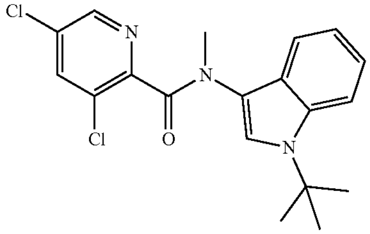

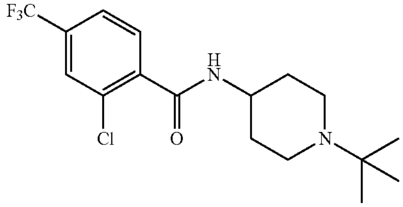

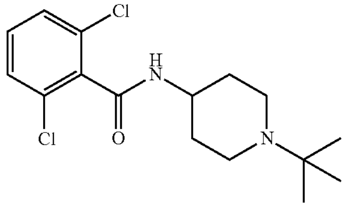

-continued

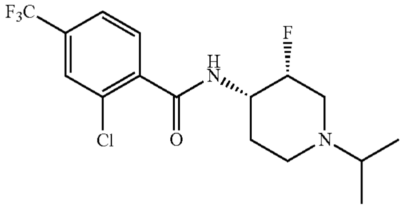

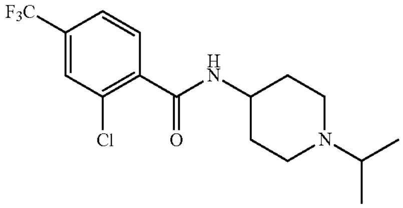

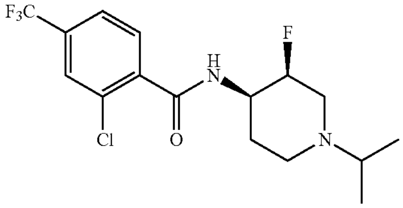

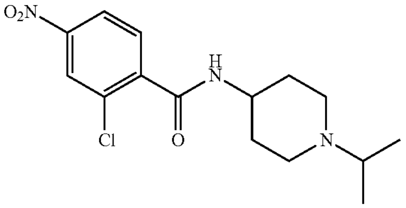

or a pharmaceutically acceptable salt thereof.

14. A method of treating an influenza infection in a subject by the administration of a composition comprising a compound of claim 1 and a pharmaceutically acceptable excipient and or a pharmaceutically acceptable salt.

15. The method of claim 14 further comprising co-administration to the subject a neuraminidase inhibitor comprising oseltamivir, zanamivir, peramivir, or any combination thereof.

* * * * *